US010429342B2

(12) United States Patent
Hoffman et al.

(10) Patent No.: US 10,429,342 B2
(45) Date of Patent: Oct. 1, 2019

(54) CHEMICALLY-SENSITIVE FIELD EFFECT TRANSISTOR

(71) Applicant: Edico Genome Corporation, La Jolla, CA (US)

(72) Inventors: Paul Hoffman, San Diego, CA (US); Mitchell Lerner, San Diego, CA (US); Pieter Van Rooyen, San Diego, CA (US)

(*) Notice: Subject to any disclaimer, the term of this patent is extended or adjusted under 35 U.S.C. 154(b) by 0 days.

(21) Appl. No.: 14/963,253

(22) Filed: Dec. 9, 2015

(65) Prior Publication Data

US 2016/0178569 A1 Jun. 23, 2016

Related U.S. Application Data

(60) Provisional application No. 62/206,228, filed on Aug. 17, 2015, provisional application No. 62/199,987, (Continued)

(51) Int. Cl.
*H01L 29/16* (2006.01)
*G01N 27/414* (2006.01)
(Continued)

(52) U.S. Cl.
CPC ..... *G01N 27/4148* (2013.01); *G01N 27/4145* (2013.01); *G01N 27/4146* (2013.01);
(Continued)

(58) Field of Classification Search
CPC ............. G01N 27/414; G01N 27/4141; G01N 27/4143; G01N 27/4145; G01N 27/4146; G01N 27/4148; H01L 29/1606
See application file for complete search history.

(56) References Cited

U.S. PATENT DOCUMENTS 3,377,893 A 4/1968 Shorb
3,466,874 A 9/1969 Holl
(Continued)

FOREIGN PATENT DOCUMENTS

CN 102703594 A 10/2012
CN 202854094 U 4/2013
(Continued)

OTHER PUBLICATIONS

Definition of "Well", http://www.merriam-webster.com (2016).*
(Continued)

*Primary Examiner* — Michele Fan
(74) *Attorney, Agent, or Firm* — Mintz Levin Cohn Ferris Glovsky and Popeo, P.C.

(57) ABSTRACT

A chemically-sensitive field effect transistor is disclosed herein. The chemically-sensitive field effect transistor comprises a CMOS structure comprising a conductive source and a conductive drain, a channel and an analyte-sensitive dielectric layer. The channel extends from the conductive source to the conductive drain. The channel is composed of a one-dimensional transistor material or a two-dimensional transistor material. The analyte-sensitive dielectric layer is disposed over the channel. An I-V curve or an I-$V_g$ curve is shifted in response to a chemical reaction occurring on or near the chemically-sensitive field effect transistor.

22 Claims, 22 Drawing Sheets

US 10,429,342 B2
Page 2

Related U.S. Application Data filed on Aug. 1, 2015, provisional application No. 62/130,594, filed on Mar. 9, 2015, provisional application No. 62/094,016, filed on Dec. 18, 2014.

(51) Int. Cl.
  *H01L 29/24* (2006.01)
  *H01L 29/778* (2006.01)

(52) U.S. Cl.
  CPC .......... *H01L 29/1606* (2013.01); *H01L 29/24* (2013.01); *H01L 29/778* (2013.01)

(56) References Cited

U.S. PATENT DOCUMENTS

| | | | |
|---|---|---|---|
| 3,564,151 | A | 2/1971 | Shlesinger, Jr. |
| 3,605,428 | A | 9/1971 | Smith et al. |
| 3,691,109 | A | 9/1972 | Larsen |
| 3,772,069 | A | 11/1973 | Daniel |
| 3,828,094 | A | 8/1974 | Widdig et al. |
| 3,892,139 | A | 7/1975 | Harris |
| 3,931,401 | A | 1/1976 | Prasad et al. |
| 5,397,863 | A | 3/1995 | Afzali-Ardakani et al. |
| 5,556,899 | A | 9/1996 | Afzali-Ardakani et al. |
| 5,571,852 | A | 11/1996 | Afzali-Ardakani et al. |
| 5,591,285 | A | 1/1997 | Afzali-Ardakani et al. |
| 5,639,660 | A | 6/1997 | Kinet et al. |
| 5,701,256 | A | 12/1997 | Marr et al. |
| 5,958,784 | A | 9/1999 | Benner |
| 6,001,611 | A | 12/1999 | Will |
| 6,377,893 | B1 | 4/2002 | Benner |
| 6,466,874 | B1 | 10/2002 | Eisenberg et al. |
| 6,564,151 | B1 | 5/2003 | Pellegrini et al. |
| 6,605,428 | B2 | 8/2003 | Kilger et al. |
| 6,691,109 | B2 | 2/2004 | Bjornson et al. |
| 6,772,069 | B1 | 8/2004 | Eisenberg et al. |
| 6,828,094 | B2 | 12/2004 | Kilger et al. |
| 6,892,139 | B2 | 5/2005 | Eisenberg et al. |
| 6,931,401 | B2 | 8/2005 | Gibson et al. |
| 7,008,764 | B1 | 3/2006 | Honold et al. |
| 7,247,877 | B2 | 7/2007 | Hakey et al. |
| 7,253,431 | B2 | 8/2007 | Afzali-Ardakani et al. |
| 7,333,980 | B2 | 2/2008 | Bjornson et al. |
| 7,462,468 | B1 | 12/2008 | Williams et al. |
| 7,484,423 | B2 | 2/2009 | Hakey et al. |
| 7,492,015 | B2 | 2/2009 | Chen et al. |
| 7,504,132 | B2 | 3/2009 | Afzali-Ardakani et al. |
| 7,514,063 | B1 | 4/2009 | Tulevski et al. |
| 7,544,546 | B2 | 6/2009 | Afzali-Ardakani et al. |
| 7,612,270 | B1 | 11/2009 | Zhu |
| 7,670,810 | B2 | 3/2010 | Gunderson et al. |
| 7,727,505 | B2 | 6/2010 | Afazali-Ardakani et al. |
| 7,732,119 | B2 | 6/2010 | Afzali-Ardakani et al. |
| 7,745,118 | B2 | 6/2010 | Green et al. |
| 7,750,908 | B2 | 7/2010 | Kincaid et al. |
| 7,761,462 | B2 | 7/2010 | Bjornson et al. |
| 7,771,695 | B2 | 8/2010 | Afzali-Ardakani et al. |
| 7,855,133 | B2 | 12/2010 | Afzali-Ardakani et al. |
| 7,867,469 | B2 | 1/2011 | Afzali-Ardakani et al. |
| 7,879,307 | B2 | 2/2011 | Afzali-Ardakani et al. |
| 7,883,685 | B1 | 2/2011 | Afzali-Ardakani et al. |
| 7,888,528 | B2 | 2/2011 | Afzali-Ardakani et al. |
| 7,917,299 | B2 | 3/2011 | Buhler et al. |
| 7,932,029 | B1 | 4/2011 | Lok |
| 7,948,015 | B2 | 5/2011 | Rothberg et al. |
| 7,951,424 | B2 | 5/2011 | Afzali-Ardakani et al. |
| 7,955,585 | B2 | 6/2011 | Afzali-Ardakani et al. |
| 7,955,931 | B2 | 6/2011 | Appenzeller et al. |
| 7,982,274 | B2 | 7/2011 | Afzali-Ardakani et al. |
| 7,993,842 | B2 | 8/2011 | McKernan et al. |
| 8,017,934 | B2 | 9/2011 | Appenzeller et al. |
| 8,032,305 | B2 | 10/2011 | Shibuya |
| 8,039,334 | B2 | 10/2011 | Furukawa et al. |
| 8,039,909 | B2 | 10/2011 | Afzali-Ardakani et al. |
| 8,057,984 | B2 | 11/2011 | Afzali-Ardakani et al. |
| 8,084,012 | B2 | 12/2011 | Afzali-Ardakani et al. |
| 8,095,508 | B2 | 1/2012 | Chamberlain et al. |
| 8,124,463 | B2 | 2/2012 | Chen et al. |
| 8,138,102 | B2 | 3/2012 | Afzali-Ardakani et al. |
| 8,138,491 | B2 | 3/2012 | Appenzeller et al. |
| 8,138,492 | B2 | 3/2012 | Afzali-Ardakani et al. |
| 8,143,030 | B2 | 3/2012 | Maxham et al. |
| 8,153,375 | B2 | 4/2012 | Travers et al. |
| 8,182,989 | B2 | 5/2012 | Bignell et al. |
| 8,182,993 | B2 | 5/2012 | Tomaney et al. |
| 8,209,130 | B1 | 6/2012 | Kennedy et al. |
| 8,211,735 | B2 | 7/2012 | Graham et al. |
| 8,211,741 | B2 | 7/2012 | Appenzeller et al. |
| 8,217,433 | B1 | 7/2012 | Fife |
| 8,227,171 | B2 | 7/2012 | Afzali-Ardakani et al. |
| 8,244,479 | B2 | 8/2012 | Kain et al. |
| 8,283,453 | B2 | 10/2012 | Afzali-Ardakani et al. |
| 8,283,703 | B2 | 10/2012 | Solomon |
| 8,293,607 | B2 | 10/2012 | Afzali-Ardakani et al. |
| 8,296,075 | B2 | 10/2012 | Den Hartog |
| 8,306,757 | B2 | 11/2012 | Rothberg et al. |
| 8,309,330 | B2 | 11/2012 | Travers et al. |
| 8,329,400 | B2 | 12/2012 | Lok |
| 8,383,345 | B2 | 2/2013 | Shendure et al. |
| 8,383,369 | B2 | 2/2013 | Maxham et al. |
| 8,394,727 | B1 | 3/2013 | Afzali-Ardakani et al. |
| 8,395,774 | B2 | 3/2013 | Afzali et al. |
| 8,445,945 | B2 | 5/2013 | Rothberg et al. |
| 8,455,193 | B2 | 6/2013 | Travers et al. |
| 8,455,297 | B1 | 6/2013 | Avouris et al. |
| 8,455,311 | B2 | 6/2013 | Solomon |
| 8,463,555 | B2 | 6/2013 | Zhang |
| 8,465,647 | B2 | 6/2013 | Bol et al. |
| 8,471,249 | B2 | 6/2013 | Chiu et al. |
| 8,481,413 | B2 | 7/2013 | Afzali-Ardakani et al. |
| 8,486,630 | B2 | 7/2013 | Pan et al. |
| 8,491,769 | B2 | 7/2013 | Afzali-Ardakani et al. |
| 8,492,293 | B1 | 7/2013 | Afzali-Ardakani et al. |
| 8,492,748 | B2 | 7/2013 | Chang et al. |
| 8,512,458 | B2 | 8/2013 | Holmes et al. |
| 8,515,682 | B2 | 8/2013 | Buhler et al. |
| 8,518,829 | B2 | 8/2013 | Dang et al. |
| 8,524,487 | B2 | 9/2013 | Fife |
| 8,535,882 | B2 | 9/2013 | Christians et al. |
| 8,546,246 | B2 | 10/2013 | Lin et al. |
| 8,554,492 | B2 | 10/2013 | Ahn et al. |
| 8,557,097 | B2 | 10/2013 | Afzali-Ardakani et al. |
| 8,558,288 | B2 | 10/2013 | Rothberg et al. |
| 8,574,892 | B2 | 11/2013 | Su |
| 8,587,065 | B2 | 11/2013 | Chen et al. |
| 8,594,951 | B2 | 11/2013 | Homer |
| 8,598,569 | B2 | 12/2013 | Afzali-Ardakani et al. |
| 8,603,792 | B2 | 12/2013 | Nikiforov et al. |
| 8,604,559 | B2 | 12/2013 | Afzali-Ardakani et al. |
| 8,609,481 | B1 | 12/2013 | Franklin et al. |
| 8,610,989 | B2 | 12/2013 | Avouris et al. |
| 8,614,436 | B2 | 12/2013 | Solomon |
| 8,617,941 | B2 | 12/2013 | Farmer et al. |
| 8,620,881 | B2 | 12/2013 | Chamberlain et al. |
| 8,628,940 | B2 | 1/2014 | Sorenson et al. |
| 8,637,374 | B2 | 1/2014 | Appenzeller et al. |
| 8,642,432 | B2 | 2/2014 | Afzali-Ardakani et al. |
| 8,674,412 | B2 | 3/2014 | Franklin et al. |
| 8,688,388 | B2 | 4/2014 | Dzakula et al. |
| 8,698,226 | B2 | 4/2014 | Jain et al. |
| 8,700,341 | B2 | 4/2014 | Rava et al. |
| 8,716,029 | B1 | 5/2014 | Kim et al. |
| 8,716,597 | B2 | 5/2014 | Mann et al. |
| 8,725,422 | B2 | 5/2014 | Halpern et al. |
| 8,738,300 | B2 | 5/2014 | Porreca et al. |
| 8,741,678 | B2 | 6/2014 | Chen et al. |
| 8,741,751 | B2 | 6/2014 | Cao et al. |
| 8,741,756 | B2 | 6/2014 | Franklin et al. |
| 8,751,166 | B2 | 6/2014 | Friedlander et al. |
| 8,751,452 | B2 | 6/2014 | Chamberlain et al. |
| 8,753,816 | B2 | 6/2014 | Rigatti et al. |
| 8,753,912 | B2 | 6/2014 | Graham et al. |
| 8,754,393 | B2 | 6/2014 | Cao et al. |
| 8,765,547 | B2 | 7/2014 | Farmer et al. |

(56) References Cited

U.S. PATENT DOCUMENTS

| | | |
|---|---|---|
| 8,766,345 B2 | 7/2014 | Farmer et al. |
| 8,772,141 B2 | 7/2014 | Afzali-Ardakani et al. |
| 8,772,910 B2 | 7/2014 | Afzali-Ardakani et al. |
| 8,779,414 B2 | 7/2014 | Chang et al. |
| 8,785,262 B2 | 7/2014 | Farmer et al. |
| 8,785,911 B2 | 7/2014 | Chen et al. |
| 8,786,018 B2 | 7/2014 | Farmer et al. |
| 8,795,961 B2 | 8/2014 | Rank et al. |
| 8,796,642 B2 | 8/2014 | Boday et al. |
| 8,796,668 B2 | 8/2014 | Lin et al. |
| 8,797,059 B2 | 8/2014 | Boday et al. |
| 8,803,129 B2 | 8/2014 | Chang et al. |
| 8,803,131 B2 | 8/2014 | Lin et al. |
| 8,803,132 B2 | 8/2014 | Farmer et al. |
| 8,805,148 B2 | 8/2014 | Avouris et al. |
| 8,809,153 B2 | 8/2014 | Afzali-Ardakani et al. |
| 8,809,837 B2 | 8/2014 | Farmer et al. |
| 8,816,328 B2 | 8/2014 | Chang et al. |
| 8,816,787 B2 | 8/2014 | Jenkins et al. |
| 8,828,762 B2 | 9/2014 | Chu et al. |
| 8,834,967 B2 | 9/2014 | Afzali-Ardakani et al. |
| 8,835,686 B2 | 9/2014 | Afzali-Ardakani et al. |
| 8,852,342 B2 | 10/2014 | Dimitrakopoulos et al. |
| 8,852,985 B2 | 10/2014 | Cai et al. |
| 8,853,034 B2 | 10/2014 | Afzali-Ardakani et al. |
| 8,859,048 B2 | 10/2014 | Afzali-Ardakani et al. |
| 8,859,439 B1 | 10/2014 | Avouris et al. |
| 8,877,340 B2 | 11/2014 | Chu et al. |
| 8,878,193 B2 | 11/2014 | Avouris et al. |
| 8,890,116 B2 | 11/2014 | Chen et al. |
| 8,890,121 B1 | 11/2014 | Han et al. |
| 8,895,372 B2 | 11/2014 | Guo et al. |
| 8,895,417 B2 | 11/2014 | Afzali-Ardakani et al. |
| 8,900,538 B2 | 12/2014 | Abou-Kandil et al. |
| 8,900,918 B2 | 12/2014 | Avouris et al. |
| 8,901,680 B2 | 12/2014 | Cai et al. |
| 8,901,689 B1 | 12/2014 | Avouris et al. |
| 8,911,972 B2 | 12/2014 | Chaisson et al. |
| 8,912,525 B2 | 12/2014 | Afzali-Ardakani et al. |
| 8,916,451 B2 | 12/2014 | Bayram et al. |
| 8,927,057 B2 | 1/2015 | Bol et al. |
| 8,932,919 B2 | 1/2015 | Farmer et al. |
| 8,936,763 B2 | 1/2015 | Rothberg et al. |
| 8,951,727 B2 | 2/2015 | Jaramillo-Botero et al. |
| 8,952,258 B2 | 2/2015 | Plucinski et al. |
| 8,957,405 B2 | 2/2015 | Adkisson et al. |
| 8,957,463 B2 | 2/2015 | Afzali-Ardakani et al. |
| 8,963,215 B2 | 2/2015 | Afzali-Ardakani et al. |
| 8,968,582 B2 | 3/2015 | Franklin et al. |
| 8,969,090 B2 | 3/2015 | Sun et al. |
| 8,969,115 B2 | 3/2015 | Chen et al. |
| 8,969,118 B2 | 3/2015 | Afzali-Ardakani et al. |
| 8,975,095 B2 | 3/2015 | Han et al. |
| 8,987,740 B2 | 3/2015 | Avouris et al. |
| 9,000,499 B2 | 4/2015 | Franklin et al. |
| 9,000,594 B2 | 4/2015 | Ott et al. |
| 9,014,989 B2 | 4/2015 | McMillen et al. |
| 9,017,813 B2 | 4/2015 | El-Ashry et al. |
| 9,029,841 B2 | 5/2015 | Farmer et al. |
| 9,040,364 B2 | 5/2015 | Farmer et al. |
| 9,045,796 B2 | 6/2015 | Gunderson et al. |
| 9,045,842 B2 | 6/2015 | Han et al. |
| 9,051,611 B2 | 6/2015 | Christians et al. |
| 9,059,188 B1 | 6/2015 | Dimitrakopoulos et al. |
| 9,062,389 B2 | 6/2015 | Han et al. |
| 9,064,698 B1 | 6/2015 | Khakifirooz et al. |
| 9,064,776 B2 | 6/2015 | Lin et al. |
| 9,064,842 B2 | 6/2015 | Bol et al. |
| 9,068,221 B2 | 6/2015 | Merriman et al. |
| 9,068,936 B2 | 6/2015 | Guo et al. |
| 9,076,873 B2 | 7/2015 | Chen et al. |
| 9,082,856 B2 | 7/2015 | Chen et al. |
| 9,085,802 B2 | 7/2015 | Liu et al. |
| 9,087,691 B2 | 7/2015 | Zhu et al. |
| 9,091,648 B2 | 7/2015 | Afzali-Ardakani et al. |
| 9,093,507 B2 | 7/2015 | Cohen et al. |
| 9,093,631 B2 | 7/2015 | Davis |
| 9,097,658 B2 | 8/2015 | Afzali-Ardakani et al. |
| 9,099,542 B2 | 8/2015 | Franklin et al. |
| 9,102,118 B2 | 8/2015 | Afzali-Ardakani et al. |
| 9,102,540 B2 | 8/2015 | Afzali-Ardakani et al. |
| 9,103,776 B2 | 8/2015 | Afzali-Ardakani et al. |
| 9,105,702 B2 | 8/2015 | Franklin et al. |
| 9,105,853 B2 | 8/2015 | Afzali-Ardakani et al. |
| 9,123,454 B2 | 9/2015 | Franklin et al. |
| 9,142,471 B2 | 9/2015 | Abou-Kandil et al. |
| 9,145,295 B2 | 9/2015 | Peng |
| 9,146,209 B2 | 9/2015 | Johnson et al. |
| 9,150,918 B2 | 10/2015 | Turner et al. |
| 9,157,887 B2 | 10/2015 | Guo et al. |
| 9,162,883 B2 | 10/2015 | El-Ashry et al. |
| 9,174,413 B2 | 11/2015 | Avouris et al. |
| 9,174,414 B2 | 11/2015 | Avouris et al. |
| 9,177,688 B2 | 11/2015 | Bol et al. |
| 9,179,579 B2 | 11/2015 | Hada et al. |
| 9,281,305 B1* | 3/2016 | Yang ............... H01L 29/41783 |
| 9,618,474 B2 | 4/2017 | van Rooyen et al. |
| 2002/0164588 A1 | 11/2002 | Eisenberg et al. |
| 2002/0194173 A1 | 12/2002 | Bjornson et al. |
| 2003/0033279 A1 | 2/2003 | Gibson et al. |
| 2003/0200033 A1 | 10/2003 | Segal et al. |
| 2003/0224384 A1 | 12/2003 | Sayood et al. |
| 2003/0228618 A1 | 12/2003 | Levanon et al. |
| 2004/0072204 A1 | 4/2004 | Shibuya |
| 2004/0110227 A1 | 6/2004 | Levanon et al. |
| 2004/0142347 A1 | 7/2004 | Stockwell et al. |
| 2004/0143571 A1 | 7/2004 | Bjornson et al. |
| 2004/0152108 A1 | 8/2004 | Keith et al. |
| 2004/0241730 A1 | 12/2004 | Yakhini et al. |
| 2004/0248189 A1 | 12/2004 | Bulaj et al. |
| 2005/0009771 A1 | 1/2005 | Levanon et al. |
| 2005/0038609 A1 | 2/2005 | Benner |
| 2005/0039123 A1 | 2/2005 | Kuchinsky et al. |
| 2005/0107961 A1 | 5/2005 | Uemura et al. |
| 2005/0131649 A1 | 6/2005 | Larsen et al. |
| 2005/0188294 A1 | 8/2005 | Kuchinsky et al. |
| 2005/0197783 A1 | 9/2005 | Kuchinsky et al. |
| 2005/0240352 A1 | 10/2005 | Liang |
| 2006/0016699 A1 | 1/2006 | Kamahori et al. |
| 2006/0028471 A1 | 2/2006 | Kincaid et al. |
| 2006/0064247 A1 | 3/2006 | Yuan et al. |
| 2006/0100788 A1 | 5/2006 | Carrino et al. |
| 2006/0106545 A1 | 5/2006 | Balaji et al. |
| 2006/0141529 A1 | 6/2006 | Koleske et al. |
| 2006/0275794 A1 | 12/2006 | Carrino et al. |
| 2006/0294059 A1 | 12/2006 | Chamberlain et al. |
| 2007/0063304 A1* | 3/2007 | Matsumoto ............ B82Y 10/00 257/462 |
| 2007/0067108 A1 | 3/2007 | Buhler et al. |
| 2007/0088510 A1 | 4/2007 | Li et al. |
| 2007/0134692 A1 | 6/2007 | Valmeekam et al. |
| 2007/0138463 A1 | 6/2007 | Herlogsson et al. |
| 2007/0152335 A1 | 7/2007 | Chun |
| 2007/0196816 A1 | 8/2007 | Schwartz et al. |
| 2007/0232060 A1 | 10/2007 | Niu |
| 2007/0259337 A1 | 11/2007 | Hully et al. |
| 2007/0277036 A1 | 11/2007 | Chamberlain et al. |
| 2008/0035494 A1 | 2/2008 | Gomez et al. |
| 2008/0063566 A1* | 3/2008 | Matsumoto ........ G01N 33/5438 422/68.1 |
| 2008/0086274 A1 | 4/2008 | Chamberlain et al. |
| 2008/0104041 A1 | 5/2008 | Bjornson et al. |
| 2008/0154567 A1 | 6/2008 | Qiu et al. |
| 2008/0250016 A1 | 10/2008 | Farrar |
| 2008/0274912 A1 | 11/2008 | Johnson et al. |
| 2008/0283875 A1* | 11/2008 | Mukasa ................ B82Y 10/00 257/253 |
| 2009/0008629 A1* | 1/2009 | Matsumoto ............ B82Y 10/00 257/24 |
| 2009/0014757 A1* | 1/2009 | Takulapalli ........ G01N 27/4145 257/253 |
| 2009/0119313 A1 | 5/2009 | Pearce |
| 2009/0125248 A1 | 5/2009 | Shams et al. |
| 2009/0153130 A1 | 6/2009 | Shim et al. |

(56) References Cited

U.S. PATENT DOCUMENTS

| | | |
|---|---|---|
| 2009/0156431 A1 | 6/2009 | Lok |
| 2009/0171647 A1 | 7/2009 | Mannava et al. |
| 2009/0278556 A1 | 11/2009 | Man et al. |
| 2009/0292665 A1 | 11/2009 | Den Hartog |
| 2009/0325239 A1 | 12/2009 | Lok |
| 2010/0025660 A1 | 2/2010 | Jain et al. |
| 2010/0035254 A1 | 2/2010 | Williams |
| 2010/0069263 A1 | 3/2010 | Shendure et al. |
| 2010/0075309 A1 | 3/2010 | Maxham et al. |
| 2010/0075327 A1 | 3/2010 | Maxham et al. |
| 2010/0077267 A1 | 3/2010 | Perego et al. |
| 2010/0082805 A1 | 4/2010 | Orton et al. |
| 2010/0088040 A1 | 4/2010 | Johnson, Jr. |
| 2010/0105202 A1 | 4/2010 | Daamen |
| 2010/0121582 A1 | 5/2010 | Pan et al. |
| 2010/0176463 A1 | 7/2010 | Koizumi et al. |
| 2010/0227384 A1 | 9/2010 | Vann |
| 2010/0228496 A1 | 9/2010 | Leong et al. |
| 2010/0293167 A1 | 11/2010 | Biasci et al. |
| 2010/0304989 A1 | 12/2010 | Von Hoff et al. |
| 2010/0327847 A1 | 12/2010 | Leiber et al. |
| 2011/0003301 A1 | 1/2011 | Raymond et al. |
| 2011/0004413 A1 | 1/2011 | Carnevali et al. |
| 2011/0042673 A1* | 2/2011 | Yamabayashi ..... G01N 27/4145 257/53 |
| 2011/0098193 A1 | 4/2011 | Kingsmore et al. |
| 2011/0121273 A1* | 5/2011 | Jo ..................... B82Y 10/00 257/40 |
| 2011/0177517 A1 | 7/2011 | Rava et al. |
| 2011/0195406 A1 | 8/2011 | Sorenson et al. |
| 2011/0201507 A1 | 8/2011 | Rava et al. |
| 2011/0210314 A1 | 9/2011 | Chung et al. |
| 2011/0212464 A1 | 9/2011 | Hagmann et al. |
| 2011/0224087 A1 | 9/2011 | Quake et al. |
| 2011/0227043 A1 | 9/2011 | Guo et al. |
| 2011/0230358 A1 | 9/2011 | Rava |
| 2011/0231446 A1 | 9/2011 | Buhler et al. |
| 2011/0237444 A1 | 9/2011 | Clancy et al. |
| 2011/0245085 A1 | 10/2011 | Rava et al. |
| 2011/0252008 A1 | 10/2011 | Chamberlain et al. |
| 2011/0257889 A1 | 10/2011 | Klammer et al. |
| 2011/0270533 A1 | 11/2011 | Zhang et al. |
| 2011/0281740 A1 | 11/2011 | Beechem et al. |
| 2011/0281768 A1 | 11/2011 | Travers et al. |
| 2011/0295514 A1 | 12/2011 | Breu et al. |
| 2011/0295858 A1 | 12/2011 | Ahn et al. |
| 2011/0295977 A1 | 12/2011 | Shibuya |
| 2011/0296543 A1 | 12/2011 | Chang et al. |
| 2012/0001615 A1 | 1/2012 | Levine |
| 2012/0010085 A1 | 1/2012 | Rava et al. |
| 2012/0011086 A1 | 1/2012 | Zhang et al. |
| 2012/0021918 A1 | 1/2012 | Bashir et al. |
| 2012/0046175 A1 | 2/2012 | Rodesch et al. |
| 2012/0046877 A1 | 2/2012 | Hyland et al. |
| 2012/0053845 A1 | 3/2012 | Bruestle et al. |
| 2012/0089339 A1 | 4/2012 | Ganeshalingam et al. |
| 2012/0094849 A1 | 4/2012 | Rava et al. |
| 2012/0095697 A1 | 4/2012 | Halpern et al. |
| 2012/0100548 A1 | 4/2012 | Rava et al. |
| 2012/0102041 A1 | 4/2012 | Park et al. |
| 2012/0109849 A1 | 5/2012 | Chamberlain et al. |
| 2012/0110316 A1 | 5/2012 | Chamberlain et al. |
| 2012/0116688 A1 | 5/2012 | Mishra et al. |
| 2012/0149582 A1 | 6/2012 | Rava et al. |
| 2012/0156677 A1 | 6/2012 | Bitinaite et al. |
| 2012/0165203 A1 | 6/2012 | Quake et al. |
| 2012/0197623 A1 | 8/2012 | Homer |
| 2012/0203792 A1 | 8/2012 | Zhang et al. |
| 2012/0208706 A1 | 8/2012 | Downing et al. |
| 2012/0214172 A1 | 8/2012 | Chen et al. |
| 2012/0214678 A1 | 8/2012 | Rava et al. |
| 2012/0220053 A1 | 8/2012 | Lee et al. |
| 2012/0221249 A1 | 8/2012 | Lizardi et al. |
| 2012/0221432 A1 | 8/2012 | Yuan et al. |
| 2012/0237928 A1 | 9/2012 | Rava et al. |
| 2012/0264121 A1 | 10/2012 | Rava et al. |
| 2012/0270739 A1 | 10/2012 | Rava et al. |
| 2012/0271558 A1 | 10/2012 | Hur et al. |
| 2012/0286244 A1 | 11/2012 | Chiu et al. |
| 2012/0289408 A1 | 11/2012 | Travers et al. |
| 2012/0289412 A1 | 11/2012 | Seitz et al. |
| 2012/0295260 A1 | 11/2012 | Pan et al. |
| 2012/0330559 A1 | 12/2012 | Jiang et al. |
| 2012/0330566 A1 | 12/2012 | Chaisson |
| 2013/0018599 A1 | 1/2013 | Peng |
| 2013/0029852 A1 | 1/2013 | Rava et al. |
| 2013/0034546 A1 | 2/2013 | Rava et al. |
| 2013/0054151 A1 | 2/2013 | Kermani et al. |
| 2013/0054508 A1 | 2/2013 | Kermani et al. |
| 2013/0059740 A1 | 3/2013 | Drmanac et al. |
| 2013/0085681 A1 | 4/2013 | Deciu et al. |
| 2013/0091126 A1 | 4/2013 | Krishnaswami et al. |
| 2013/0091176 A1 | 4/2013 | Harris et al. |
| 2013/0096011 A1 | 4/2013 | Rava et al. |
| 2013/0096841 A1 | 4/2013 | Kermani et al. |
| 2013/0103320 A1 | 4/2013 | Dzakula et al. |
| 2013/0124100 A1 | 5/2013 | Drmanac et al. |
| 2013/0137588 A1 | 5/2013 | Shendure et al. |
| 2013/0137605 A1 | 5/2013 | Shendure et al. |
| 2013/0138355 A1 | 5/2013 | Inglis et al. |
| 2013/0138358 A1 | 5/2013 | Tang et al. |
| 2013/0140518 A1 | 6/2013 | Jain et al. |
| 2013/0150253 A1 | 6/2013 | Deciu et al. |
| 2013/0157870 A1 | 6/2013 | Pushkarev et al. |
| 2013/0164859 A1 | 6/2013 | Johnson et al. |
| 2013/0166221 A1 | 6/2013 | Inglis et al. |
| 2013/0184161 A1 | 7/2013 | Kingsmore et al. |
| 2013/0190211 A1 | 7/2013 | Bustillo et al. |
| 2013/0091121 A1 | 8/2013 | Bhola et al. |
| 2013/0194882 A1 | 8/2013 | Ishii et al. |
| 2013/0204851 A1 | 8/2013 | Bhola et al. |
| 2013/0211729 A1 | 8/2013 | Sastry-Dent et al. |
| 2013/0230909 A1 | 9/2013 | Pan et al. |
| 2013/0237432 A1 | 9/2013 | Li et al. |
| 2013/0240378 A1 | 9/2013 | Lee et al. |
| 2013/0245958 A1 | 9/2013 | Forster |
| 2013/0251726 A1 | 9/2013 | Mascola et al. |
| 2013/0261983 A1 | 10/2013 | Dzakula et al. |
| 2013/0273543 A1 | 10/2013 | Gudmundsson et al. |
| 2013/0288244 A1 | 10/2013 | Deciu et al. |
| 2013/0288901 A1 | 10/2013 | Kennedy et al. |
| 2013/0296175 A1 | 11/2013 | Rafnar et al. |
| 2013/0297221 A1 | 11/2013 | Johnson et al. |
| 2013/0304392 A1 | 11/2013 | Deciu et al. |
| 2013/0307029 A1 | 11/2013 | Xu et al. |
| 2013/0309666 A1 | 11/2013 | Deciu et al. |
| 2013/0309678 A1 | 11/2013 | Travers et al. |
| 2013/0310260 A1 | 11/2013 | Kim et al. |
| 2013/0311106 A1 | 11/2013 | White et al. |
| 2013/0316331 A1 | 11/2013 | Isakov et al. |
| 2013/0316915 A1 | 11/2013 | Halpern et al. |
| 2013/0316916 A1 | 11/2013 | Flusberg et al. |
| 2013/0324417 A1 | 12/2013 | Kennedy et al. |
| 2013/0324419 A1 | 12/2013 | Seshagiri |
| 2013/0325360 A1 | 12/2013 | Deciu et al. |
| 2013/0325666 A1 | 12/2013 | Carrino et al. |
| 2013/0332081 A1 | 12/2013 | Reese et al. |
| 2013/0338012 A1 | 12/2013 | Sulem et al. |
| 2013/0338933 A1 | 12/2013 | Deciu et al. |
| 2013/0338934 A1 | 12/2013 | Asadi et al. |
| 2013/0345066 A1 | 12/2013 | Brinza et al. |
| 2014/0024536 A1 | 1/2014 | Richards et al. |
| 2014/0024541 A1 | 1/2014 | Richards et al. |
| 2014/0024542 A1 | 1/2014 | Richards et al. |
| 2014/0025312 A1 | 1/2014 | Chin et al. |
| 2014/0031240 A1 | 1/2014 | Behlke et al. |
| 2014/0033125 A1 | 1/2014 | Meral |
| 2014/0034880 A1 | 2/2014 | Blouin et al. |
| 2014/0038830 A1 | 2/2014 | Srinivasan et al. |
| 2014/0045705 A1 | 2/2014 | Bustamante et al. |
| 2014/0051154 A1 | 2/2014 | Hyland et al. |
| 2014/0051588 A9 | 2/2014 | Drmanac et al. |
| 2014/0053294 A1 | 2/2014 | Gresshoff |
| 2014/0066317 A1 | 3/2014 | Talasaz |

(56) References Cited

U.S. PATENT DOCUMENTS

| | | |
|---|---|---|
| 2014/0067830 A1 | 3/2014 | Buhler et al. |
| 2014/0087961 A1 | 3/2014 | Sulem et al. |
| 2014/0100792 A1 | 4/2014 | Deciu et al. |
| 2014/0114582 A1 | 4/2014 | Mittelman et al. |
| 2014/0121116 A1 | 5/2014 | Richards et al. |
| 2014/0122509 A1 | 5/2014 | Pantaleoni et al. |
| 2014/0129201 A1 | 5/2014 | Kennedy et al. |
| 2014/0134629 A1 | 5/2014 | Turner et al. |
| 2014/0148346 A1 | 5/2014 | Spormann et al. |
| 2014/0149049 A1 | 5/2014 | Chen et al. |
| 2014/0152291 A1 | 6/2014 | Afzali-Ardakani et al. |
| 2014/0155298 A1 | 6/2014 | Von Hoff et al. |
| 2014/0156199 A1 | 6/2014 | Von Hoff et al. |
| 2014/0162278 A1 | 6/2014 | Richards et al. |
| 2014/0163900 A1 | 6/2014 | Erlich et al. |
| 2014/0166487 A1 | 6/2014 | Lieber et al. |
| 2014/0172319 A1 | 6/2014 | Von Hoff et al. |
| 2014/0173606 A1 | 6/2014 | Pantaleoni |
| 2014/0193938 A1 | 7/2014 | Fife |
| 2014/0200166 A1 | 7/2014 | Van Rooyen et al. |
| 2014/0209982 A1 | 7/2014 | Putnam et al. |
| 2014/0236490 A1 | 8/2014 | McMillen et al. |
| 2014/0248692 A1 | 9/2014 | Lagace et al. |
| 2014/0249052 A1 | 9/2014 | Mehmet et al. |
| 2014/0260547 A1 | 9/2014 | Balandin |
| 2014/0264467 A1 | 9/2014 | Cheng et al. |
| 2014/0264469 A1 | 9/2014 | Fife et al. |
| 2014/0274774 A1 | 9/2014 | Li et al. |
| 2014/0297196 A1 | 10/2014 | Olson |
| 2014/0309944 A1 | 10/2014 | McMillen et al. |
| 2014/0315199 A1 | 10/2014 | Rhodes et al. |
| 2014/0363808 A1 | 12/2014 | Gu et al. |
| 2014/0371109 A1 | 12/2014 | McMillen et al. |
| 2014/0371110 A1 | 12/2014 | Van Rooyen et al. |
| 2015/0065353 A1 | 3/2015 | Turner et al. |
| 2015/0069329 A1 | 3/2015 | Jeon et al. |
| 2015/0087534 A1 | 3/2015 | Gormley et al. |
| 2015/0101931 A1 | 4/2015 | Garaj et al. |
| 2015/0111759 A1 | 4/2015 | Ju et al. |
| 2015/0123080 A1* | 5/2015 | Yamaguchi ....... H01L 29/42368 257/29 |
| 2015/0137078 A1 | 5/2015 | Guo et al. |
| 2015/0159196 A1 | 6/2015 | Travers et al. |
| 2015/0159212 A1 | 6/2015 | Pantoja et al. |
| 2015/0160159 A1 | 6/2015 | Afzali-Ardakani et al. |
| 2015/0176071 A1 | 6/2015 | Fisher et al. |
| 2015/0211054 A1 | 7/2015 | Kostem et al. |
| 2015/0218630 A1 | 8/2015 | Sun et al. |
| 2015/0225785 A1 | 8/2015 | Zhao et al. |
| 2015/0232929 A1 | 8/2015 | Stephens et al. |
| 2015/0233864 A1 | 8/2015 | Shen et al. |
| 2015/0239947 A1 | 8/2015 | Brinkmann et al. |
| 2015/0243917 A1 | 8/2015 | Kim et al. |
| 2015/0259743 A1 | 9/2015 | Urgess et al. |
| 2015/0302143 A1 | 10/2015 | Ma et al. |
| 2015/0302144 A1 | 10/2015 | Chin et al. |
| 2015/0307936 A1 | 10/2015 | Goldsmith |
| 2015/0307947 A1 | 10/2015 | Basu et al. |
| 2015/0308977 A1 | 10/2015 | Saito et al. |
| 2015/0339437 A1 | 11/2015 | McMillen et al. |
| 2015/0368638 A1 | 12/2015 | Steemers et al. |
| 2016/0004298 A1 | 1/2016 | Mazed et al. |
| 2016/0122792 A1 | 5/2016 | Peterson et al. |
| 2016/0171153 A1 | 6/2016 | Van Rooyen et al. |
| 2016/0180019 A1 | 6/2016 | Van Rooyen et al. |
| 2016/0231251 A1 | 8/2016 | Ou et al. |
| 2016/0265047 A1 | 9/2016 | van Rooyen et al. |
| 2017/0018626 A1 | 1/2017 | Hoffman et al. |
| 2017/0053908 A1 | 2/2017 | Hoffman |
| 2017/0059514 A1 | 3/2017 | Hoffman |
| 2017/0102358 A1 | 4/2017 | Hoffman |
| 2017/0218442 A1 | 8/2017 | van Rooyen et al. |

FOREIGN PATENT DOCUMENTS

| | | |
|---|---|---|
| CN | 103293209 A | 9/2013 |
| CN | 104237352 A | 12/2014 |
| DE | 19813317 A1 | 9/1999 |
| EP | 2163646 A1 | 3/2010 |
| EP | 2334802 A1 | 6/2011 |
| EP | 2535429 A1 | 12/2012 |
| EP | 3 235 010 A1 | 10/2017 |
| JP | 2004085392 A * | 3/2004 |
| JP | 2010172290 A | 8/2010 |
| WO | WO-99/049403 A1 | 9/1999 |
| WO | WO-00/045322 A1 | 8/2000 |
| WO | WO-01/13432 A1 | 2/2001 |
| WO | WO-02/090978 A1 | 11/2002 |
| WO | WO-03/046220 A1 | 6/2003 |
| WO | WO-2004/029298 A2 | 4/2004 |
| WO | WO-2004/090100 A2 | 10/2004 |
| WO | WO-2004/104161 A2 | 12/2004 |
| WO | WO-2005/026925 A2 | 3/2005 |
| WO | WO-2005/029059 A1 | 3/2005 |
| WO | WO-2005/048134 A2 | 5/2005 |
| WO | WO-2005/090961 A1 | 9/2005 |
| WO | WO-2005/113812 A2 | 12/2005 |
| WO | WO-2006/015084 A2 | 2/2006 |
| WO | WO-2006/019892 A2 | 2/2006 |
| WO | WO-2006/096324 A2 | 9/2006 |
| WO | WO-2007/064758 A2 | 6/2007 |
| WO | WO-2007/076726 A1 | 7/2007 |
| WO | WO-2008/022036 A2 | 2/2008 |
| WO | WO-2008/098014 A2 | 8/2008 |
| WO | WO-2008/127213 A2 | 10/2008 |
| WO | WO-2008/143679 A2 | 11/2008 |
| WO | WO-2008/156773 A1 | 12/2008 |
| WO | WO-2009/035647 A1 | 3/2009 |
| WO | WO-2009/120372 A2 | 10/2009 |
| WO | WO-2009/143212 A1 | 11/2009 |
| WO | WO-2010/003316 A1 | 1/2010 |
| WO | WO-2010/027497 A2 | 3/2010 |
| WO | WO-2010/036287 A1 | 4/2010 |
| WO | WO-2010/036311 A2 | 4/2010 |
| WO | WO-2010/051773 A1 | 5/2010 |
| WO | WO-2010/072382 A1 | 7/2010 |
| WO | WO-2010/093465 A1 | 8/2010 |
| WO | WO-2010/127045 A2 | 11/2010 |
| WO | WO-2010/129019 A2 | 11/2010 |
| WO | WO-2010/129301 A2 | 11/2010 |
| WO | WO-2010/132814 A1 | 11/2010 |
| WO | WO-2011/025819 A1 | 3/2011 |
| WO | WO-2011/050341 A1 | 4/2011 |
| WO | WO-2011/056688 A2 | 5/2011 |
| WO | WO-2011/063210 A2 | 5/2011 |
| WO | WO-2011/071923 A2 | 6/2011 |
| WO | WO-2011/082178 A1 | 7/2011 |
| WO | WO-2011/090556 A1 | 7/2011 |
| WO | WO-2011/090557 A1 | 7/2011 |
| WO | WO-2011/090558 A1 | 7/2011 |
| WO | WO-2011/090559 A1 | 7/2011 |
| WO | WO-2011/091046 A1 | 7/2011 |
| WO | WO-2011/091063 A1 | 7/2011 |
| WO | WO-2011/095501 A1 | 8/2011 |
| WO | WO-2011/137368 A2 | 11/2011 |
| WO | WO-2011/139797 A2 | 11/2011 |
| WO | WO-2011/143525 A2 | 11/2011 |
| WO | WO-2011/145954 A1 | 11/2011 |
| WO | WO-2011/145955 A1 | 11/2011 |
| WO | WO-2012/006291 A2 | 1/2012 |
| WO | WO-2012/029080 A1 | 3/2012 |
| WO | WO-2012/051346 A1 | 4/2012 |
| WO | WO-2012/058459 A2 | 5/2012 |
| WO | WO-2012/065228 A1 | 5/2012 |
| WO | WO-2012/066582 A1 | 5/2012 |
| WO | WO-2012/085948 A2 | 6/2012 |
| WO | WO-2012/092336 A2 | 7/2012 |
| WO | WO-2012/092426 A1 | 7/2012 |
| WO | WO-2012/095872 A1 | 7/2012 |
| WO | WO-2012/101643 A1 | 8/2012 |
| WO | WO-2012/123972 A1 | 9/2012 |
| WO | WO-2012/142334 A2 | 10/2012 |

(56) References Cited

FOREIGN PATENT DOCUMENTS

| | | |
|---|---|---|
| WO | WO-2012/142531 A2 | 10/2012 |
| WO | WO-2012/168803 A2 | 12/2012 |
| WO | WO-2012/168815 A2 | 12/2012 |
| WO | WO-2012/170715 A1 | 12/2012 |
| WO | WO-2012/172575 A1 | 12/2012 |
| WO | WO-2012/177774 A2 | 12/2012 |
| WO | WO-2012/177792 A2 | 12/2012 |
| WO | WO-2013/043909 A1 | 3/2013 |
| WO | WO-2013/052907 A2 | 4/2013 |
| WO | WO-2013/052913 A2 | 4/2013 |
| WO | WO-2013/055817 A1 | 4/2013 |
| WO | WO-2013/058907 A1 | 4/2013 |
| WO | WO-2013/062856 A1 | 5/2013 |
| WO | WO-2013/065072 A1 | 5/2013 |
| WO | WO-2013/067167 A2 | 5/2013 |
| WO | WO-2013/080227 A1 | 6/2013 |
| WO | WO-2013/088457 A1 | 6/2013 |
| WO | WO-2013/109935 A1 | 7/2013 |
| WO | WO-2013/109981 A1 | 7/2013 |
| WO | WO-2013/119770 A1 | 8/2013 |
| WO | WO-2013/123330 A1 | 8/2013 |
| WO | 2013128371 | 9/2013 |
| WO | WO-2013/148400 A1 | 10/2013 |
| WO | WO-2013/166517 A1 | 11/2013 |
| WO | WO-2013/177086 A1 | 11/2013 |
| WO | WO-2013/177581 A2 | 11/2013 |
| WO | WO-2013/184643 A1 | 12/2013 |
| WO | WO-2013/192562 A1 | 12/2013 |
| WO | WO-2014/008447 A1 | 1/2014 |
| WO | WO-2014/012051 A1 | 1/2014 |
| WO | WO-2014/014497 A1 | 1/2014 |
| WO | WO-2014/014498 A1 | 1/2014 |
| WO | WO-2014/014950 A1 | 1/2014 |
| WO | WO-2014/015084 A2 | 1/2014 |
| WO | WO-2014/015319 A1 | 1/2014 |
| WO | WO-2014/018093 A1 | 1/2014 |
| WO | WO-2014/024041 A1 | 2/2014 |
| WO | WO-2014/024598 A1 | 2/2014 |
| WO | WO-2014/026168 A1 | 2/2014 |
| WO | WO-2014/036488 A1 | 3/2014 |
| WO | WO-2014/039556 A1 | 3/2014 |
| WO | WO-2014/041380 A1 | 3/2014 |
| WO | 2014060305 | 4/2014 |
| WO | WO-2014/052909 A2 | 4/2014 |
| WO | WO-2014/055774 A1 | 4/2014 |
| WO | 2014074246 | 5/2014 |
| WO | WO-2014/071070 A1 | 5/2014 |
| WO | WO-2014/071279 A2 | 5/2014 |
| WO | WO-2014/078739 A1 | 5/2014 |
| WO | WO-2014/089241 A2 | 6/2014 |
| WO | WO-2014/112199 A1 | 7/2014 |
| WO | WO-2014/142850 A1 | 9/2014 |
| WO | WO-2014/153188 A2 | 9/2014 |
| WO | WO-2014/166535 A1 | 10/2014 |
| WO | WO-2014/171969 A1 | 10/2014 |
| WO | WO-2014/172046 A2 | 10/2014 |
| WO | WO-2014/176524 A2 | 10/2014 |
| WO | WO-2015/033229 A2 | 3/2015 |
| WO | WO-2015/123444 A2 | 8/2015 |
| WO | WO-2016/205253 A1 | 12/2016 |

OTHER PUBLICATIONS

International Search Report for PCT Application No. PCT/US2015/064848, dated Mar. 31, 2016.

Basu et al., Recent Advances in Carbon Nanotubes Based Biosensors, Sensors, 8:1-x manuscripts, downloaded from: http://www.mdpi.org/sensors/accepted/sensors-util-24-21-malhorta-in-PRE-PUBLISHED-VERSION-0422.pdf (Jan. 31, 2008).

Cooper et al., Experimental Review of Graphene, ISRN Condensed Matter Physics 2012: Art. ID 501686, 56 pages. (2012).

DeVolder et al., Carbon Nanotubes: Present and Future Commercial Applications, Science, 339: 535-539 (Feb. 1, 2013).

Fakih et al., Large area graphene ion sensitive field effect transistors with tantalum pentoxide sensing layers for pH measurement at the Nernstian limit, Applied Physics Letters 105: 083101 (Aug. 25, 2014).

Gao et al., The new age of carbon nanotubes: An updated review of functionalized carbon nanotubes in electrochemical sensors, Nanoscale 4:1948 (2012).

Green et al., Interactions of DNA with graphene and sensing applications of graphene field-effect transistor devices: A review, Analytica Chimica Acta 853:127-142 (2015).

Kim, Lecture Notes, 2.76/2.760 Multiscale Systems Design & Manufacturing, downloaded from: http://ocw.mit.edu/courses/mechanical-engineering/2-76-multi-scale-system-design-fall-2004/lecture-notes/lecture_15.pdf (Fall 2004).

Park et al., High-density integration of carbon nanotubes via chemical self-assembly, Nature Nanotechnology 7:787-791 (2012).

Schwierz, Frank; Graphene Transistors, Nature Nanotechnology 5:487-496 (May 30, 2010).

Tulevski et al., Toward High-Performance Digital Logic Technology with Carbon Nanotubes, ACS Nano 8(9):8730-8745 (Aug. 21, 2014).

Zhan et al., Graphene Field-Effect Transistor and Its Application for Electronic Sensing, Small 10(20):4042-4065 (Aug. 29, 2014).

Cheng, Zengguang et al. "Sensitivity Limits and Scaling of Bioelectronic Graphene Transducers.", *Nano Letters*, (2013), pp. 2902-2907, 13(6), ACS Publications.

Cheng, Zengguang et al. "Supporting Information for: Sensitivity Limits and Scaling of Bioelectronic Graphene Transducers.", (2013), 26 pages, pubs.acs.org. [retrieved from the Internet on Nov. 7, 2017].

Cheng, Zengguang et al. "Suspended Graphene Sensors with Improved Signal and Reduced Noise." *Nano Letters*, (2010), pp. 1864-1868, 10(5), pubs.acs.org.

Kim, Kihyun et al. "Electrical and pH Sensing Characteristics of Si Nanowire-Based Suspended FET Biosensors." *Proceedings of the 14th IEEE, International Conference on Nanotechnology*, IEEE, (Aug. 18-21, 2014), pp. 768-771.

Kim, Kihyun et al. "Suspended honeycomb nanowire ISFETs for improved stiction-free performance." *Nanotechnology*, (2014), pp. 345-501 (7 pages), 25(34), IOP Publishing, Bristol, GB.

Wang, Bei et al. "Oxide-on-graphene field effect bio-ready sensors." *Nano Research*, (2014), 7(9):pp. 1263-1270. Tsinghua University Press, CN.

Xu et al. "Electrophoretic and field-effect graphene for all-electrical DNA array technology." Nature Communications, (2014) 5:4866. 9 pages.

Liu, Song and Xuefeng Guo, "Carbon nanomaterials field-effect-transistor-based biosensors." NPG Asia Materials (2012), pp. 1-10, 4, e23; doi: 10.1038/sm.2012.42: published online Aug. 17, 2012.

Baraket, Mira et al. (2008) "Aminated graphene for DNA attachment produced via plasma functionalization", Applied Physics Letters, A I P Publishing LLC, US, vol. 100, No. 23, Jun. 4, 2012 (Jun. 4, 2012) pp. 233123-233123-4, XP012156487, ISSN: 0003-6951, DOI: 10.1063/1.4711771 [retrieved on Jun. 8, 2012].

Schwierz, Frank, J. Pezoldt and R. Granzner, "Two-dimensional materials and their prospect in transistor electonics." Nanoscale, 2015, 7, pp. 8261-8283.

\* cited by examiner

CHEMICALLY-SENSITIVE FIELD EFFECT TRANSISTOR

CROSS REFERENCES TO RELATED APPLICATIONS

The present application claims priority to U.S. Provisional Patent Application No. 62/206,228, filed on Aug. 17, 2015, U.S. Provisional Patent Application No. 62/199,987, filed on Aug. 1, 2015, U.S. Provisional Patent Application No. 62/130,594, filed on Mar. 9, 2015, and U.S. Provisional Patent Application No. 62/094,016, filed on Dec. 18, 2014, all of which are hereby incorporated by reference in their entireties.

STATEMENT REGARDING FEDERALLY SPONSORED RESEARCH OR DEVELOPMENT

Not Applicable

BACKGROUND OF THE INVENTION

Field of the Invention

The present invention generally relates to field effect transistors. More specifically, the present invention relates to one dimensional and two dimensional field effect transistors.

Description of the Related Art

The sequencing of Nucleic Acids, such as deoxyribonucleic acid (DNA), is a fundamental part of biological discovery. Such detection is useful for a variety of purposes and is often used in scientific research as well as medical advancement. For instance, the genomics and bioinformatics fields are concerned with the application of information technology and computer science to the field of molecular biology. In particular, bioinformatics techniques can be applied to process and analyze various genomic data, such as from an individual so as to determine qualitative and quantitative information about that data that can then be used by various practitioners in the development of diagnostic, prophylactic, and/or therapeutic methods for detecting, preventing or at least ameliorating diseased states, and thus, improving the safety, quality, and effectiveness of health care. The need for such diagnostic, therapeutic, and prophylactic advancements has led to a high demand for low-cost sequencing, which in turn has driven the development of high-throughput sequencing, termed as Next generation sequencing (NGS).

Generally, the approach to DNA analysis, such as for genetic diagnostics and/or sequencing, involves nucleic acid hybridization and detection. For example, various typical hybridization and detection approaches include the following steps. For genetic analysis, an RNA or DNA sample of a subject to be analyzed may be isolated and immobilized on a substrate, a probe of a known genetic sequence, e.g., a disease marker, may be labeled and washed across the substrate. If the disease marker is present, a binding event will occur, e.g., hybridization, and because the probe has been labeled the hybridization event may either be or not be detected thereby indicating the presence or absence of the disease marker in the subject's sample.

For DNA sequencing, first, an unknown nucleic acid sequence to be identified, e.g., a single-stranded sequence of DNA of a subject, is isolated, amplified, and immobilized on a substrate. Next, a known nucleic acid labeled with an identifiable tag is contacted with the unknown nucleic acid sequence in the presence of a polymerase. When hybridization occurs, the labeled nucleic acid binds to its complementary base in the unknown sequence immobilized on the surface of the substrate. The binding event can then be detected, e.g., optically or electrically. These steps are then repeated until the entire DNA sample has been completely sequenced. Typically, these steps are performed by a Next Gen Sequencer wherein thousands to millions of sequences may concurrently be produced in the next-generation sequencing process.

For example, a central challenge in DNA sequencing is assembling full-length genomic sequences, e.g., chromosomal sequences, from a sample of genetic material and/or mapping and aligning sample sequence fragments to a reference genome, yielding sequence data in a format that can be compared to a reference genomic sequence such as to determine the variants in the sampled full-length genomic sequences. In particular, the methods employed in sequencing protocols do not produce full-length chromosomal sequences of the sample DNA.

Rather, sequence fragments, typically from 100-1,000 nucleotides in length, are produced without any indication as to where in the genome they align. Therefore, in order to generate full length chromosomal genomic constructs, or determine variants with respect to a reference genomic sequence, these fragments of DNA sequences need to be mapped, aligned, merged, and/or compared to a reference genomic sequence. Through such processes the variants of the sample genomic sequences from the reference genomic sequences may be determined.

However, as the human genome is comprised of approximately 3.1 billion base pairs, and as each sequence fragment is typically only from 100 to 500 to 1,000 nucleotides in length, the time and effort that goes into building such full length genomic sequences and determining the variants therein is quite extensive often requiring the use of several different computer resources applying several different algorithms over prolonged periods of time.

In a particular instance, thousands to millions of fragments or even billions of DNA sequences are generated, aligned, and merged in order to construct a genomic sequence that approximates a chromosome in length. A step in this process may include comparing the DNA fragments to a reference sequence to determine where in the genome the fragments align.

The genetic material must be pre-processed, so as to derive usable genetic sequence data. This preprocessing may be done manually or via an automated sequencer. Typically, preprocessing involves obtaining a biological sample from a subject, such as through venipuncture, hair, etc. and treating the sample to isolate the DNA therefrom. Once isolated the DNA may be denatured, strand separated, and/or portions of the DNA may then be multiplied, e.g., via polymerase chain reaction (PCR), so as to build a library of replicated strands that are now ready to be read, such as by an automated sequencer, which sequencer is configured to read the replicate strands, e.g., by synthesis, and thereby determine the nucleotide sequences that makes up the DNA. Further, in various instances, such as in building the library of replicated strands, it may be useful to provide for over-coverage when preprocessing a given portion of the DNA. To perform this over-coverage, e.g., using PCR, may require increased sample preparation resources and time, and therefore be more expensive, but it often gives an enhanced probability of the end result being more accurate.

Once the library of replicated strands has been generated they may be injected into an automated sequencer that may then read the strands, such as by synthesis, so as to determine the nucleotide sequences thereof. For instance, the replicated single stranded DNA may be attached to a glass bead and inserted into a test vessel, e.g., an array. All the necessary components for replicating its complementary strand, including labeled nucleotides, are also added to the vessel but in a sequential fashion. For example, all labeled "A", "C", "G", and "T's" are added, either one at a time or all together to see which of the nucleotides is going to bind at position one. After each addition a light, e.g., a laser, is shone on the array. If the composition fluoresces then an image is produced indicating which nucleotide bound to the subject location. More particularly, where the nucleotides are added one at a time, if a binding event occurs, then its indicative fluorescence will be observed. If a binding event does not occur, the test vessel may be washed and the procedure repeated until the appropriate one of the four nucleotides binds to its complement at the subject location, and its indicative fluorescence is observed. Where all four nucleotides are added at the same time, each may be labeled with a different fluorescent indicator, and the nucleotide that binds to its complement at the subject position may be determined, such as by the color of its fluorescence. This greatly accelerates the synthesis process.

Once a binding event has occurred, the complex is then washed and the synthesis steps are repeated for position two. For example, a marked nucleotide "A" may be added to the mix to determine if the complement at the position is a "T", and if so, all the sequences having that complement will bind to the labeled "T" and will therefore fluoresce, and the samples will all be washed. Where the binding happened the bound nucleotide is not washed away, and then this will be repeated for all nucleotides for all positions until all the over-sampled nucleic acid segments, e.g., reads, have been sequenced and the data collected. Alternatively, where all four nucleotides are added at the same time, each labeled with a different fluorescent indicator, only one nucleotide will bind to its complement at the subject position, and the others will be washed away, such that after the vessel has been washed, a laser may be shone on the vessel and which nucleotide bound to its complement may be determined, such as by the color of its fluorescence.

This continues until the entire strand has been replicated in the vessel. Usually a typical length of a sequence replicated in this manner is from about 100 to about 500 base pairs, such as between 150 to about 400 base pairs, including from about 200 to about 350 base pairs, such as about 250 base pairs to about 300 base pairs dependent on the sequencing protocol being employed. Further, the length of these segments may be predetermined, e.g., engineered, to accord with any particular sequencing machinery and/or protocol by which it is run. The end result is a readout, or read, that is comprised of a replicated DNA segment, e.g., from about 100 to about 1,000 nucleotides in length, that has been labeled in such a manner that every nucleotide in the sequence, e.g., read, is known because of its label. Hence, since the human genome is comprised of about 3.2 billion base pairs, and various known sequencing protocols usually result in labeled replicated sequences, e.g., reads, from about 100 or 101 bases to about 250 or about 300 or about 400 bases, the total amount of segments that need to be sequenced, and consequently the total number of reads generated, can be anywhere from about 10,000,000 to about 40,000,000, such as about 15,000,000 to about 30,000,000, dependent on how long the label replicated sequences are.

Therefore, the sequencer may typically generate about 30,000,000 reads, such as where the read length is 100 nucleotides in length, so as to cover the genome once.

However, in part, due to the need for the use of optically detectable, e.g., fluorescent, labels in the sequencing reactions being performed, the required instrumentation for performing such high throughput sequencing is bulky, costly, and not portable. For this reason, a number of new approaches for direct, label-free detection of DNA sequencing have been proposed. For instance, among the new approaches are detection methods that are based on the use of various electronic analytic devices. Such direct electronic detection methods have several advantages over the typical NGS platform. For example, the detector may be incorporated in the substrate itself, such as employing a biosystem-on-a-chip device, such as a complementary metal oxide semiconductor device, "CMOS". More particularly, in using a CMOS device in genetic detection, the output signal representative of a hybridization event can be directly acquired and processed on a microchip. In such an instance, automatic recognition is achievable in real time and at a lower cost than is currently achievable using NGS processing. Moreover, standard CMOS devices may be employed for such electronic detection making the process simple, inexpensive, and portable.

Particularly, in order for next-generation sequencing to become widely used as a diagnostic in the healthcare industry, sequencing instrumentation will need to be mass produced with a high degree of quality and economy. One way to achieve this is to recast DNA sequencing in a format that fully leverages the manufacturing base created for computer chips, such as complementary metal-oxide semiconductor (CMOS) chip fabrication, which is the current pinnacle of large scale, high quality, low-cost manufacturing of high technology. To achieve this, ideally the entire sensory apparatus of the sequencer could be embodied in a standard semiconductor chip, manufactured in the same fab facilities used for logic and memory chips. Recently, such a sequencing chip, and the associated sequencing platform, has been developed and commercialized by Ion Torrent, a division of Thermo-Fisher, Inc. The promise of this idea has not been realized commercially due to the fundamental limits of applying a metal oxide semiconductor field effect transistor, or MOSFET, as a bio sensor. When a MOSFET is used in solution as a biosensor, it is referred to as an ISFET. A particular limitation includes a lack of sensor sensitivity and signal to noise characteristics as the semiconductor node scales down to lower geometries of the transistor (gate length).

More particularly, a field effect transistor, FET, typically includes a gate, a channel region connecting source and drain electrodes, and an insulating barrier separating the gate from the channel. The operation of a conventional FET relies on the control of the channel conductivity, and thus the drain current, by a voltage, $V_{GS}$, applied between the gate and source. For high-speed applications, and for the purposes of increasing sensor sensitivity, FETs should respond quickly to variations in $V_{GS}$. However, this requires short gates and fast carriers in the channel. Unfortunately, FETs with short gates frequently suffer from degraded electrostatics and other problems (collectively known as short channel effects), such as threshold-voltage roll-off, drain-induced barrier lowering, and impaired drain-current saturation, which results in a decrease in sensor sensitivity. Nevertheless, scaling theory predicts that a FET with a thin barrier and a thin gate-controlled region (measured in the vertical direction) will be robust against short-channel effects down to very short gate lengths (measured in the horizontal direction).

Accordingly, the possibility of having channels that are very thin in the vertical dimension would allow for high-speed transmission of carriers as well as for increased sensor sensitivity and accuracy. What is needed, therefore, is a FET device that is configured in such a manner as to include a shorter gate than is currently achievable in present FET applications. A solution that includes such a FET device designed for use in biological applications, such as for nucleic acid sequencing and/or genetic diagnostics would especially be beneficial.

BRIEF SUMMARY OF THE INVENTION

The present invention is a chemically-sensitive field-effect transistor that solves many of the current problems associated with nucleic acid sequencing and genetic diagnostics.

One aspect of the present invention is a chemically-sensitive field effect transistor. The chemically-sensitive field effect transistor comprises an integrated circuit structure comprising a conductive source and a conductive drain and a channel. The channel extends from the conductive source to the conductive drain. The channel is composed of a one-dimensional transistor material or a two-dimensional transistor material. An I-V curve or an I-$V_g$ curve is shifted in response to a chemical reaction occurring on or near the chemically-sensitive field effect transistor.

Another aspect of the present invention is a bio-sensor. The bio-sensor includes a semiconductor structure comprising a conductive source and a conductive drain, a 2D material channel (e.g. a graphene channel) or a 1D material channel (e.g. a Carbon NanoTube (CNT)) extending from the source to the drain and a well structure positioned on or over a portion of an exterior surface or topmost portion of the channel. The 1D or 2D material comprising the channel may be covered by a dielectric layer or may have no covering such that the well structure defines an opening allowing for direct contact with the either the dielectric layer or the 1D or 2D material channel. An I-$V_g$ curve is shifted in response to detection of a biological compound.

Yet another aspect of the present invention is a 1D or 2D material field effect transistor such as a graphene field effect transistor or GFET. The GFET includes a structure comprising a conductive source, a conductive drain, and a graphene channel extending from the source to the drain. An I-$V_g$ curve is shifted in response to a chemical reaction occurring on the graphene field effect transistor.

Yet another aspect of the present invention is a chemically-sensitive field effect transistor comprising an integrated circuit structure, a channel and an oxide layer. The integrated circuit structure comprises a conductive source and a conductive drain. The channel extends from the conductive source to the conductive drain. The channel is composed of a one-dimensional transistor material or a two-dimensional transistor material. The oxide layer is disposed over the channel. The I-V curve or an I-Vg curve is shifted in response to a chemical reaction occurring over or near the chemically-sensitive field effect transistor.

Yet another aspect of the present invention is a bio-sensor comprising a complementary metal-oxide-semiconductor ("CMOS") structure, a graphene channel, an oxide layer, and a well structure. The CMOS structure comprises a damascene copper source and a damascene copper drain. The graphene channel extends from the source to the drain. The oxide layer is disposed over the graphene channel and has a thickness of 50 nanometers or less. The well structure is positioned over a portion of an exterior surface of the oxide layer. The well structure defines an opening allowing for direct contact with the oxide layer. An I-V or I-Vg curve is shifted in response to detection of a biological compound.

Yet another aspect of the present invention is a graphene field effect transistor comprising a CMOS structure, a graphene channel, an oxide layer, and a well structure. The CMOS structure comprises a copper source and a copper drain. The graphene channel extends from the source to the drain. The oxide layer is disposed over the graphene channel and has a thickness of 50 nanometers or less. The well structure is positioned over a portion of an exterior surface of the oxide layer. The well structure defines an opening allowing for direct contact with the oxide layer. An I-V or I-Vg curve is shifted in response to detection of a biological compound.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

As shown in FIGS. 1, 2, 3 and 4, an embodiment of the present invention is a chemically-sensitive field effect transistor that comprises an integrated circuit structure comprising a conductive source and a conductive drain and a channel. The channel extends from the conductive source to the conductive drain. An I-V curve or an I-$V_g$ curve is shifted in response to a chemical reaction occurring on or near the chemically-sensitive field effect transistor.

Figure 5:
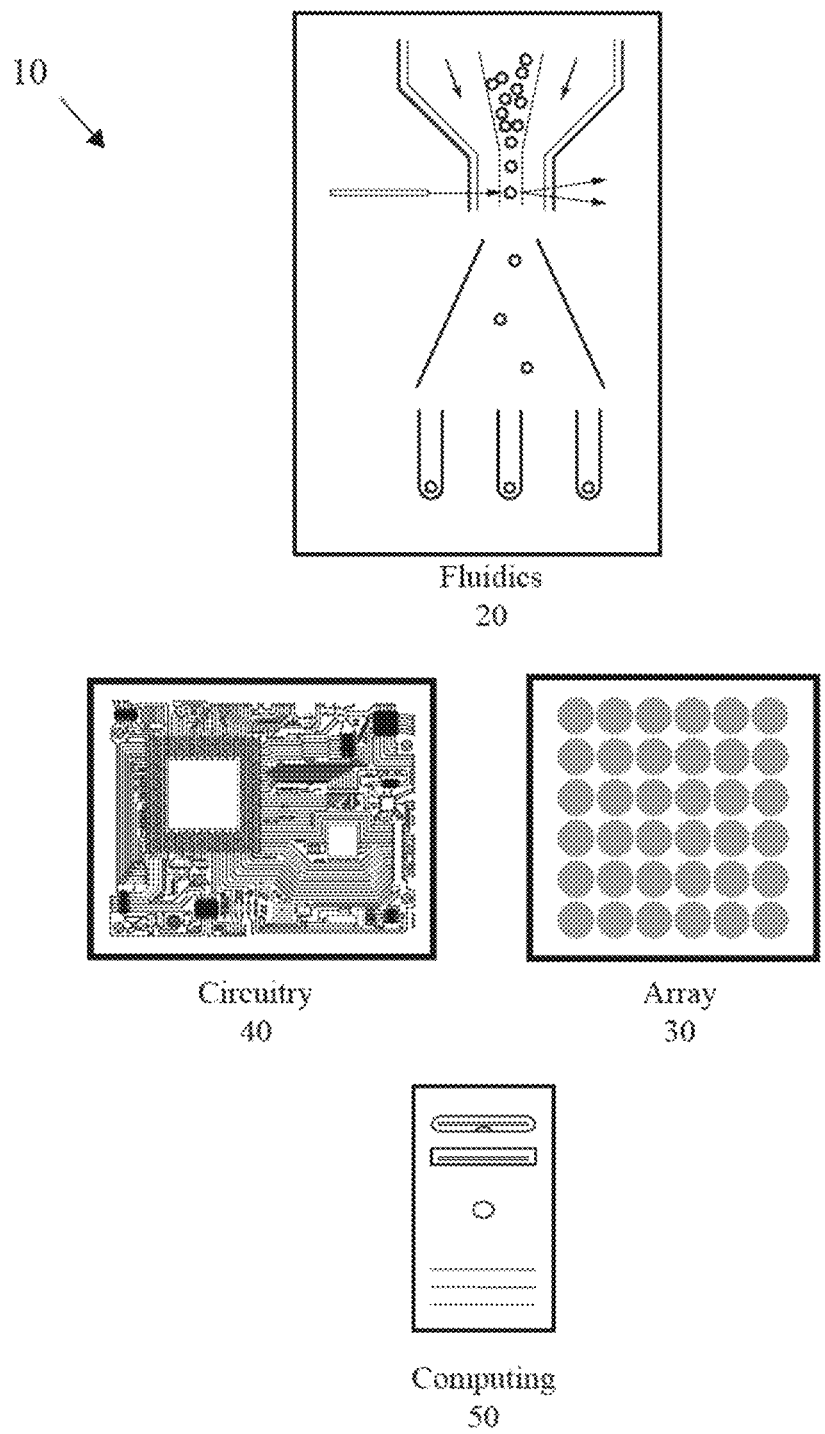
FIG. 5 is a block diagram of a system for analysis of biological or chemical materials.

As shown in FIG. 5, a system for analysis of biological or chemical materials is generally designated 10. The biological material is preferably a nucleic acid, other biological molecule, protein, or the like. The analysis is performed for whole genome analysis, genome typing analysis, genomic panels, exome analysis, micro-biome analysis, and clinical analysis. The clinical analysis comprises cancer analysis, NIPT analysis or UCS analysis. The system 10 preferably includes a fluidics component 20, an array 30 of sensors, a circuitry component 40 and a computing component 50. The system 10 also preferably includes at least a reference electrode. The fluidics component 20 is used to deliver reagents to the array of sensors and may comprise reagent supplies connected by tubing to the array of sensors 30. The fluidics component 20 comprises valves, manifolds or other flow control structures to tightly administer the composition, amount, timing and duration of fluid flow in the system.

Figure 1:
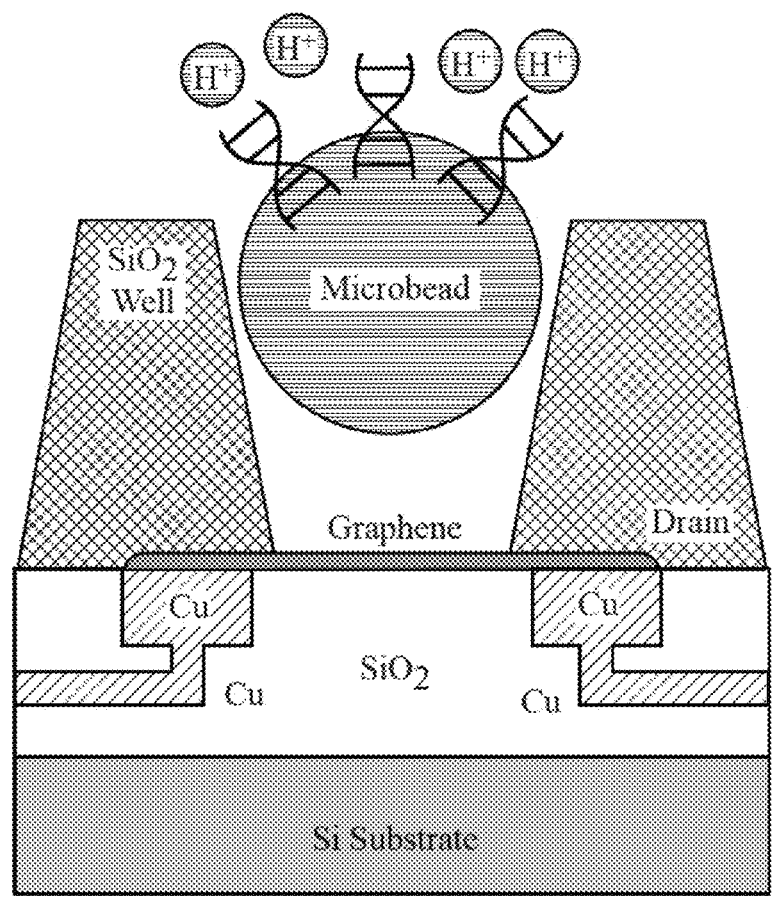
FIG. 1 is a cross-section diagram of a chemically-sensitive field-effect transistor utilized for analysis of biological or chemical materials.

As shown in FIGS. 1-4, the chemically-sensitive field-effect transistor 32 preferably includes a conductive source, a conductive drain, and a channel extending from the conductive source to the conductive drain. The conductive source and conductive drain are provided by a conductive element 34, such as a wiring trace or electrode. Depending on the fabrication process common semiconductor wiring trace materials are copper or aluminum—although others are known in the art such as gold or platinum. It is advantageous to match the work function of the conductive element 34 with the material comprising the channel 33. The preferred embodiment has conductive elements 34 with a work function compatible with graphene (e.g. Pt is a good choice) and with a contact structure that provides the lowest contact resistance possible. Although FIG. 1 shows the conductive elements 34 (source and drain) contacting the channel from the bottom, it is also possible for the conductive elements to contact the channel from the top. It is further possible that in some designs it would be preferable for one conductive element 34 (source or drain) to contact the channel from one direction while the complementary conductive element (drain or source, respectively) contacts the channel from the opposing direction. The actual contact from the conductive element 34 to the channel 33 may be with the conductive element 34 contacting a surface of the channel 33. Alternatively the conductive element 34 may be structured as a via that extends through the material of the channel 33—thus contacting the channel on a perimeter of the hole through the channel 33. Furthermore intermediate materials may be used to enhance the contact from the conductive material 34 to the channel 33.

The channel 33 overlies a lower dielectric layer 37. $SiO_2$ is a common dielectric used in semiconductor fabrication and can be used for this purpose. Alternatively other materials may be chosen that due to their structure allow the chemically-sensitive FET to operate at a high level (e.g. have enhanced mobility in the channel). In a preferred embodiment where the channel 33 is comprised of graphene the lower dielectric layer 37 is comprised of hexagonal boron nitride (hBN). Since both hBN and graphene have a hexagonal crystal lattice structure with very similar lattice spacing—the hBN does not distort the graphene lattice—thus allowing for higher carrier mobility in the graphene.

Figure 7:
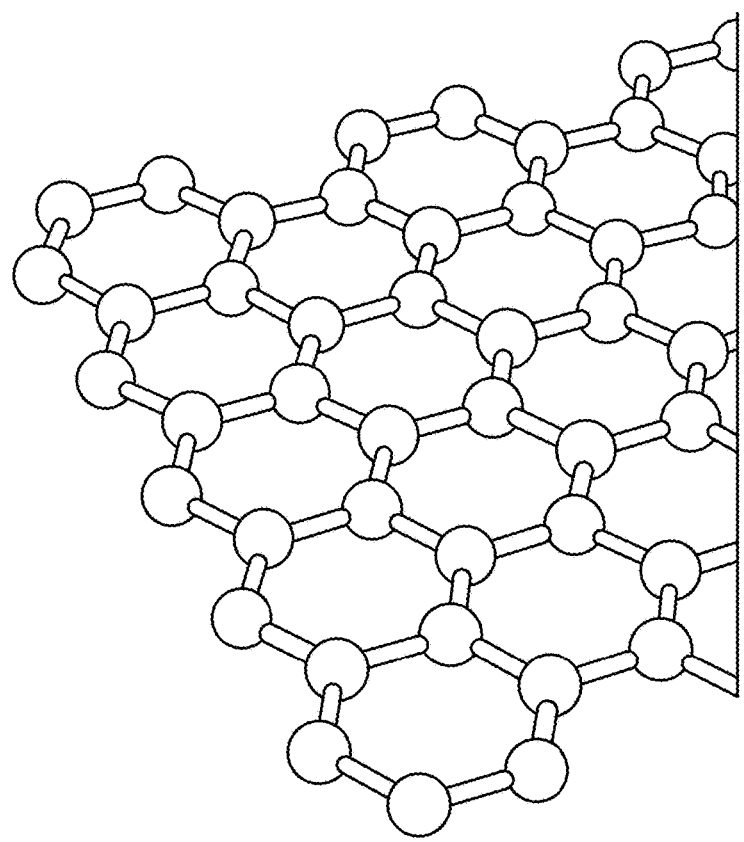
FIG. 7 is an illustration of graphene.
Figure 17:
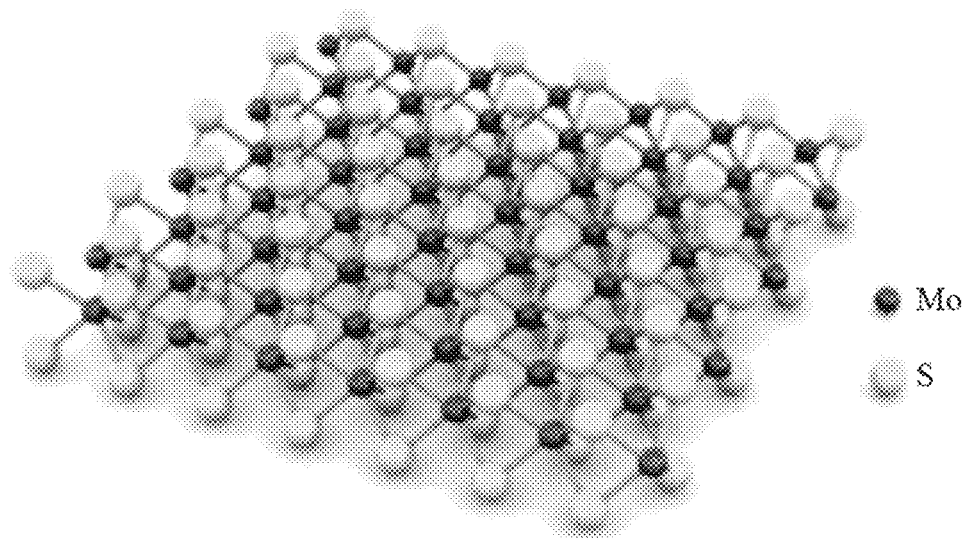
FIG. 17 is an illustration of molybdenum disulfide.
Figure 18:
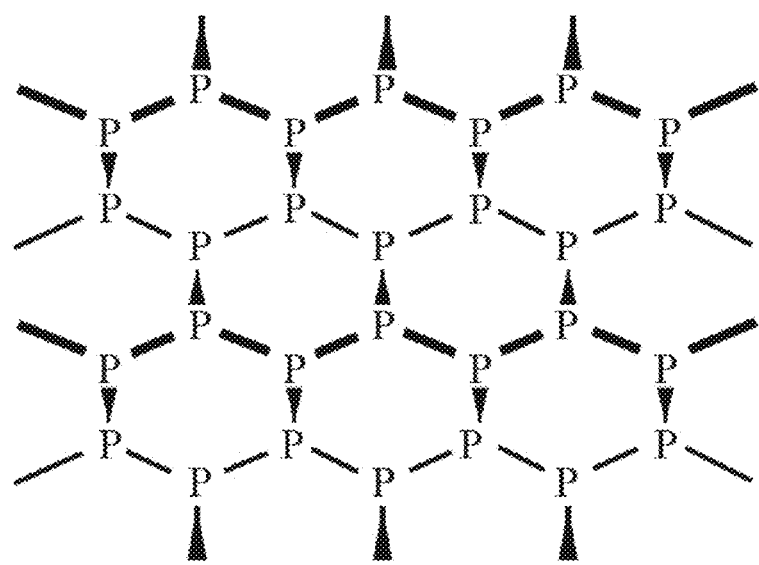
FIG. 18 is an illustration of black phosphorous.
Figure 19:
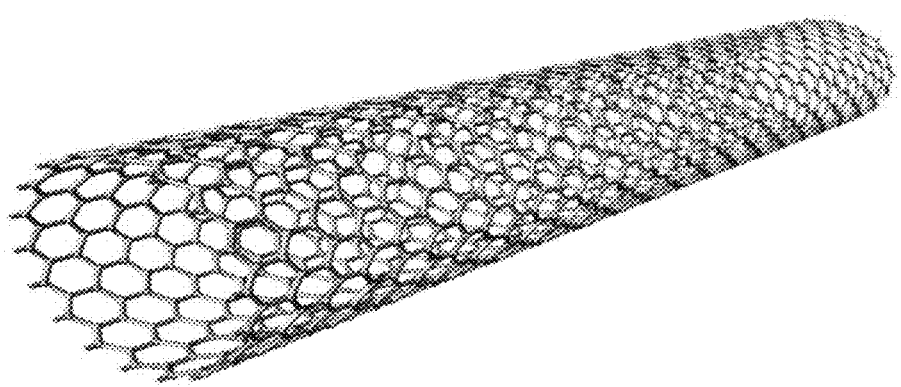
FIG. 19 is an illustration of a nanotube.
Figure 20:
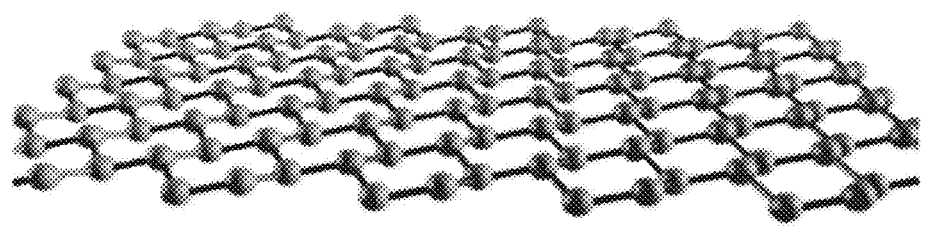
FIG. 20 is an illustration of silicene.
Figure 21:
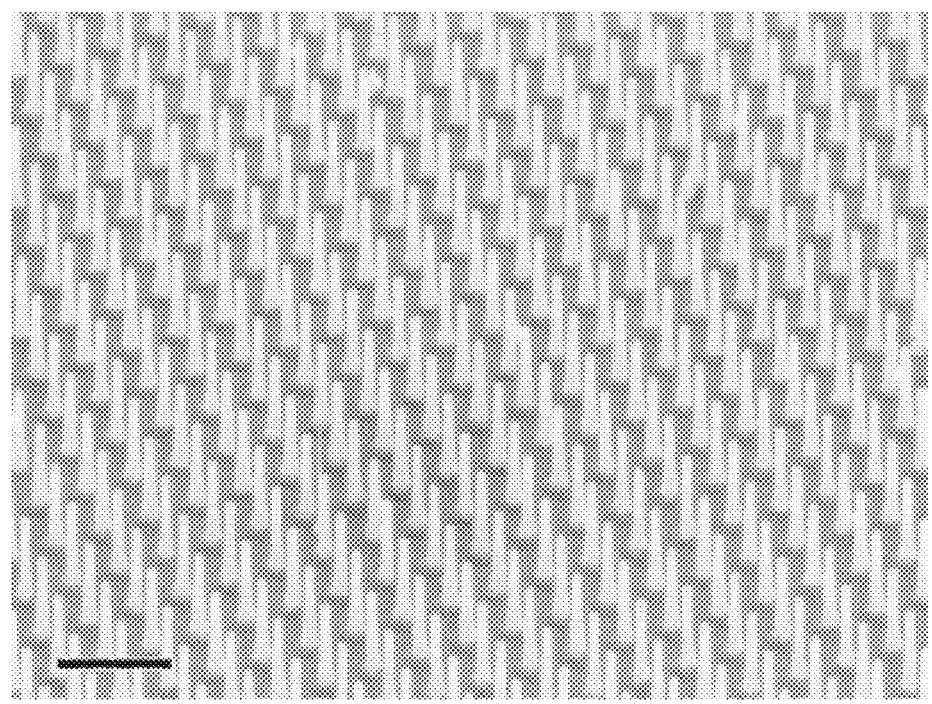
FIG. 21 is an illustration of a semiconductor nanowire structure.

The channel 33 is preferably composed of a one-dimensional transistor material or a two-dimensional transistor material. In a preferred embodiment the two-dimensional material is graphene, as shown FIG. 7. In another preferred embodiment the one-dimensional material is one or more Carbon NanoTubes (CNTs), as shown in FIG. 19. To achieve the best transistor transconductance (which relates to the sensitivity of the sensors in the sensor array 30) it is preferred to have the shorted channel length possible. A preferred length of the channel 33 from the source to the drain ranges is less than 1 micron, and more preferably is less than 500 nm, and more preferably is less than 50 nm, and more preferably still is as short as the fabrication process will allow without generating defects or results that render the device unusable. The most preferable channel length will be 20 nm or less. An alternative length is 0.05 micron to 3 microns. Conversely, the preferred width of the channel is as wide as possible. The width of the channel 33 in this case is not governed by the fabrication process as much as by the design requirements of the overall sensor chip. It is likely that many millions of sensors will be desired on the sensor chip. With this large number of sensors the individual sensor size and pitch (which directly affects the channel width) must be kept reasonably small otherwise the chip will so large as to be unable to be fabricated (e.g. exceeds the photolithography reticle size) or too expensive (due to the effect of defect density on a large chip size). A practical range of channel width is from 0.1 micron to 2 microns. An alternative width is 0.05 micron to 2 microns. In some cases it is desirable to increase the channel length to channel width ratio through the use of design techniques—for example, an interdigitated tooth and comb design can provide for short channel lengths and large channel widths within a relatively compact area. The channel 33 is preferably composed of a two-dimensional transistor material such as graphene, molybdenum disulfide (as shown in FIG. 17), other metal dichalcogenides, and black phosphorous (as shown in FIG. 18). Alternatively, the channel 33 is composed of a one-dimensional transistor material such as a carbon nanotube or a semiconductor nanowire (as shown in FIG. 21). Alternatively, the channel is composed of a silicene, as shown in FIG. 20. Additional alternative materials for the channel include borophene, WS2, boron nitride, stanene (2D tin), germanane, nickel HITP, and Mxenes (Ti2C, (Ti0.5, Nb0.5), V2C, Nb2C, Ti3C2, Ti3CN, Nb4C3 and Ta4C3). The most preferred material is graphene (FIG. 7).

Graphene is a two-dimensional mono layer of carbon atoms that form a lattice structure. The molecular structure of graphene, however, is very unique in that each carbon atom shares one of its four free valence electrons with three of its adjacent and planar carbon atoms such that each of the three planar carbon atoms is orientated at about a 120° with respect to the other three carbon atoms. This orientation gives graphene a honeycomb, lattice structure. Additionally, the fourth valence electron forms a pi bond, perpendicular to the three planar sigma-bonded carbon atoms, which is responsible for the unique electronic characteristics of graphene.

A single-layer graphene is a two-dimensional material. Its lattice structure forms regular hexagons with a carbon atom at each vertex. The bond length between adjacent carbon atoms is about 1.42 Å and the lattice constant is about 2.46 Å. This structure gives graphene two important characteristics: it makes graphene a semimetal (no bandgap) and it promotes rapid charge transport (mobility and high-field transport) at room temperature. Hence, in various instances, a graphene FET (G-FET or GFET used interchangeably), as herein described may perform better as a biological sensor then a typical CMOS-FET device. For instance, with respect to hybridization detection and/or sequencing, a traditional MOSFET transistor may have fundamental limitations in its sensitivity (due to channel thickness and intervening insulating layers), whereas a GFET has a single atom thickness channel that can be in direct contact or very close proximity with a chemical reaction zone. Furthermore graphene (or other 1D or 2D transistors) has a much higher carrier mobility than the doped silicon used in a MOSFET or IS_FET. This gives the herein disclosed GFETs increased sensitivity to and faster detection of chemical reactions.

Figure 1A:
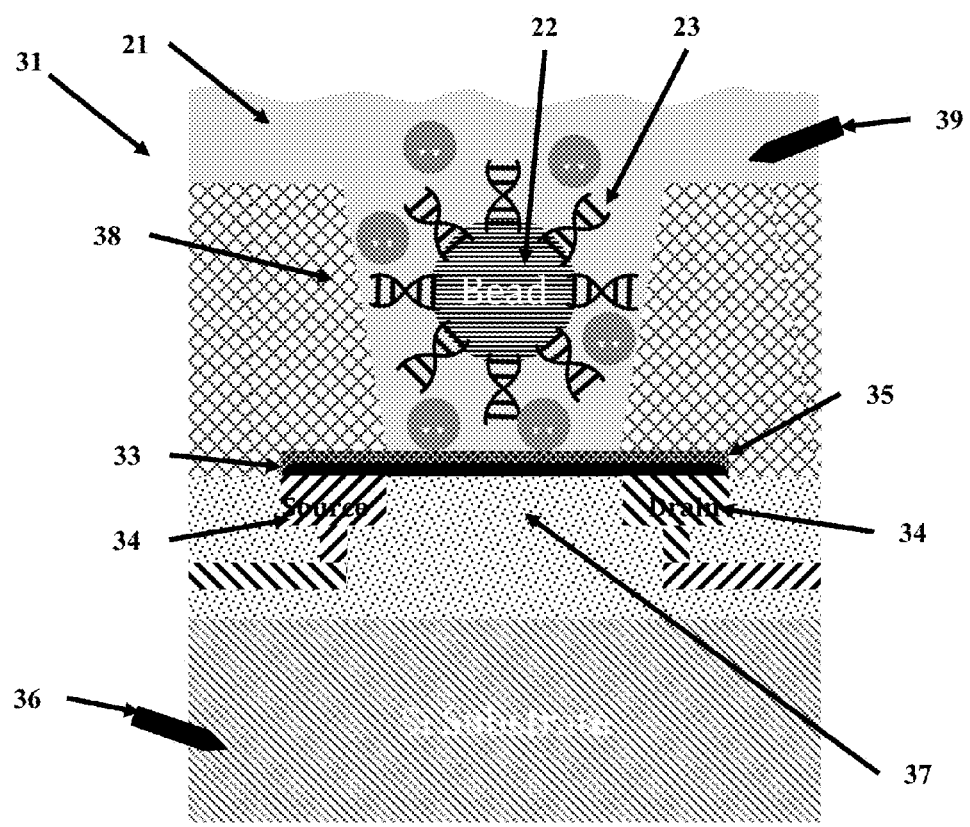
FIG. 1A is a cross-section diagram of a chemically-sensitive field-effect transistor utilized for analysis of biological or chemical materials.
Figure 2:
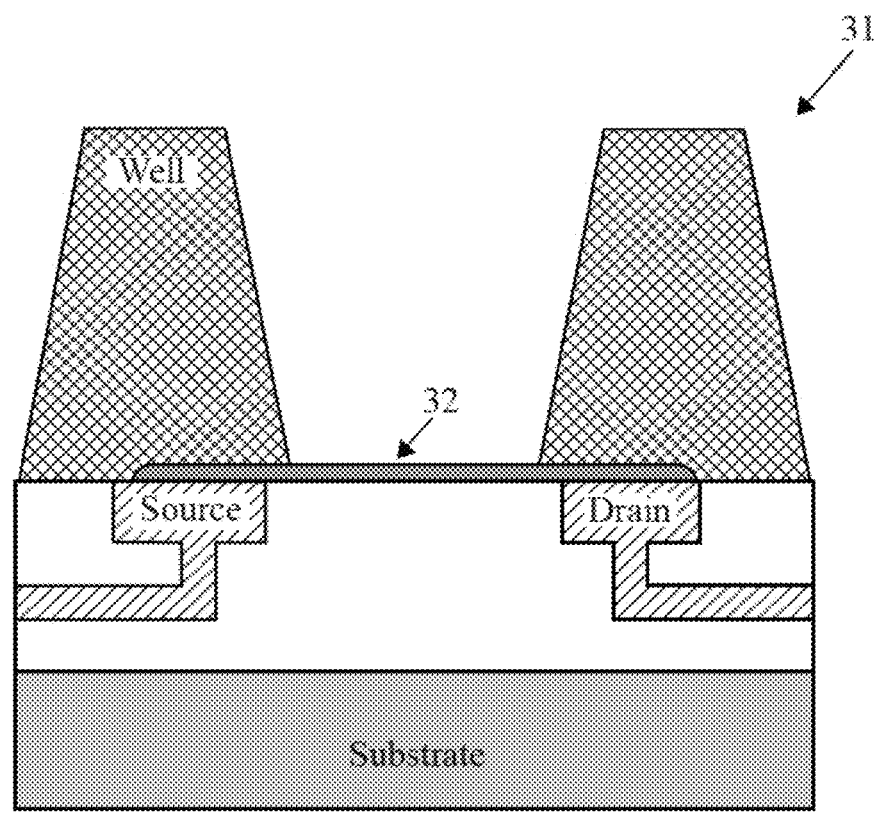
FIG. 2 is a cross-section diagram of a chemically-sensitive field-effect transistor with a well structure.
Figure 2A:
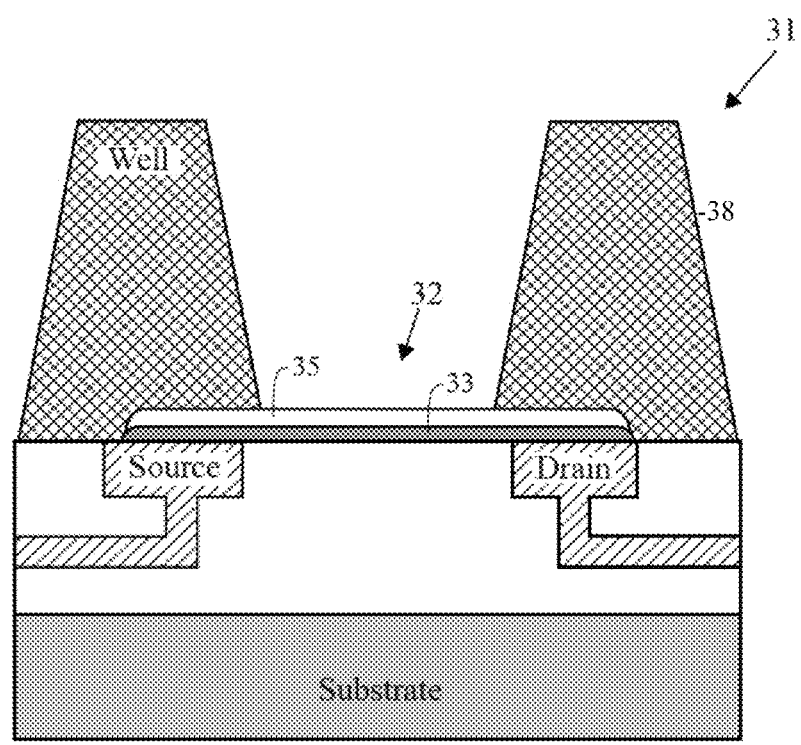
FIG. 2A is a cross-section diagram of a chemically-sensitive field-effect transistor with a well structure.
Figure 3:
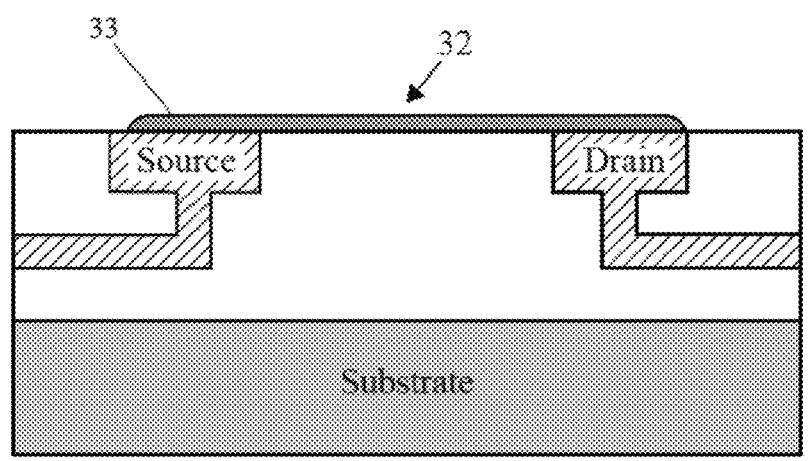
FIG. 3 is a cross-section diagram of a chemically-sensitive field-effect transistor.
Figure 3A:
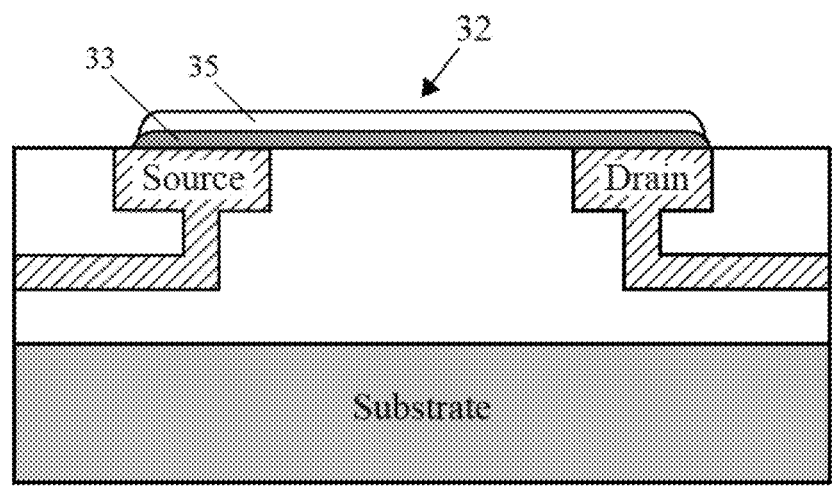
FIG. 3A is a cross-section diagram of a chemically-sensitive field-effect transistor.
Figure 4:
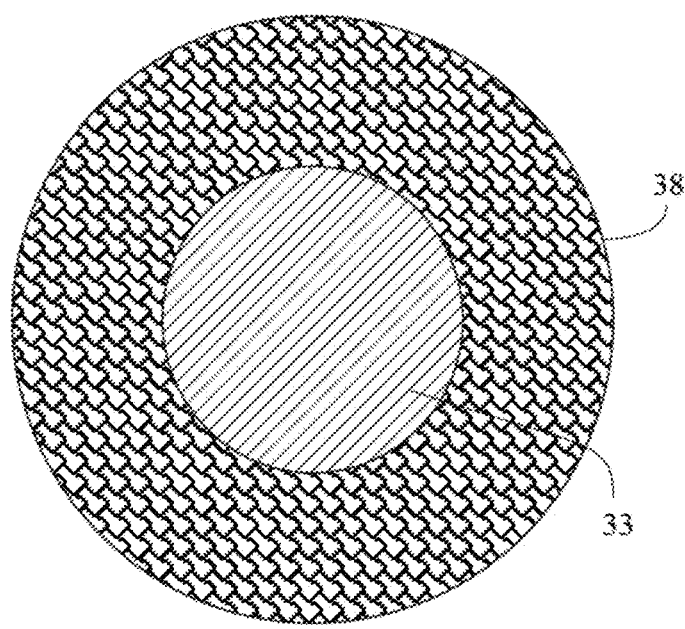
FIG. 4 is a top plan view of a chemically-sensitive field-effect transistor with a well structure.

As shown in FIGS. 1A, 2A and 3A, a preferred embodiment of the chemically-sensitive field-effect transistor 32 preferably includes a dielectric layer (or oxide layer) 35 that covers the channel material. This dielectric layer 35 may be chosen because it is sensitive to a particular analyte of interest and so we can describe this as an analyte-sensitive dielectric layer 35. For example, during DNA sequencing, when a base nucleotide combines with its complementary base pair a hydrogen ion is released. The ability to detect the hydrogen ion release (or a plurality of such releases) by the chemically-sensitive FET sensor can be enhanced by having a layer that is particularly sensitive to the ion or analyte of interest—in this case hydrogen ions. Dielectric materials can be chosen for their hydrogen ion sensitivity in addition to their compatibility with fabrication processes. Some hydrogen ion sensitive dielectrics include tantalum oxide ($Ta_2O_5$), hafnium oxide ($HfO_2$), aluminum oxide ($Al_2O_3$), titanium oxide ($TiO_2$), hafnium silicate, zirconium silicate, zirconium dioxide, lanthanum oxide, titanium oxide, iron oxide, or yttrium oxide, and others. A preferred material for the analyte-sensitive dielectric layer 35 is tantalum oxide ($Ta_2O_5$). The analyte-sensitive dielectric layer 35 is preferably thinner than 150 nm, and more preferably thinner than 60 nm, and most preferably thinner than 30 nm. In an alternative embodiment, the analyte-sensitive dielectric layer 35 is comprised of two or more analyte-sensitive dielectric layer layers. If an etching process is used to define the well structures 38, it can be desirable for the analyte-sensitive dielectric layer 35 to have a high etch selectivity in comparison to the material of the well layer 38—in this case acting as an etch stop for the well etch. It may be difficult to deposit a dielectric material onto clean graphene since there are in the ideal case no bonds available on the graphene surface to bond to. The deposition process must have a component whereby initial adhesion of the deposited analyte-sensitive dielectric layer 35 is insured. This may be done by some appropriate physical or chemical pre-treatment of the graphene surface or by the addition of a pre-cursor layer (e.g. a deposit or spun-on polymer) prior to the deposition of the analyte-sensitive dielectric layer. A preferred method for depositing the dielectric layer 35 comprises Atomic Layer Deposition (ALD). In some embodiments an analyte-sensitive dielectric layer 35 will neither be required nor used.

Preferably, a well structure 38 is positioned on or over a portion of an exterior surface of the analyte-sensitive dielectric layer 35 which in turn is on or over the channel 33 of a sensor 31, and the well structure defines an opening allowing for direct contact with the analyte-sensitive dielectric layer 35. The well structure 38 is preferably composed of an insulator material. The insulator material for the well structure is preferably an inorganic material, such as silicon oxide or silicon nitride. Alternatively, the insulator material for the well structure is an organic material such as a polyimide, a benzocyclobutene ("BCB") material, or other like materials. If an organic material is used it is preferably a photosensitive material so that it can be photo-imaged and developed directly without the need for a photoresist material. The size (diameter or equivalent width), shape and depth of the well must be matched to the size range of microbeads carrying DNA template strands. It is preferred that the well geometry only allows the possibility for one bead to be entrapped in the well.

As shown in FIG. 1A, a microbead is positioned within the well structure in proximity to the analyte-sensitive layer 35 and thereby near to the channel 38. For DNA sequencing the microbead has a plurality of DNA template strands that cover its surface and if the bead is porous or a gel material the DNA template strands may be throughout the bead material.

Figure 6:
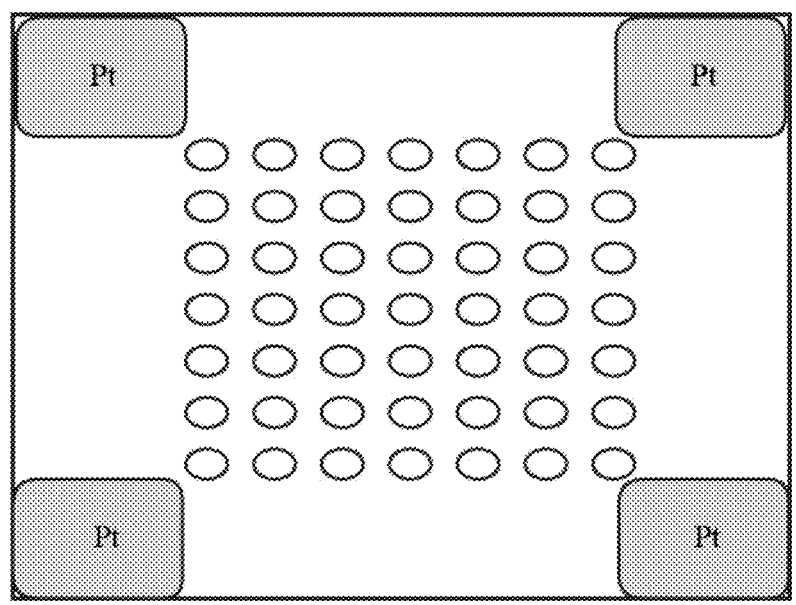
FIG. 6 is a top plan view of an array comprising multiple chemically-sensitive field-effect transistors.

As shown in FIG. 6, an array 30 comprises a plurality of sensors. It is further possible that the reference electrode for supplying the solution gate voltage can be incorporated as part of the sensor chip or within the package holding the sensor chip. Reference electrodes are preferably comprised of platinum or Ag/AgCl.

FIG. 1A shows a solution-gate electrode 39 to supply the solution gate voltage to the fluid or solution. This is an electrode that is in electrical communication with the fluid at some point in the fluidics system 20 or within the chip package or over the chip. This solution gate 39 is sometimes referred to as a top or front gate. FIG. 1A additionally shows the option of providing a back gate 36 (sometimes referred to as a bottom gate). In this case the back gate voltage can be applied through a highly-doped and relatively conductive semiconductor substrate. An array of back gate 36 structures could also be constructed from an array of Through-Silicon-Vias (TSVs) that could bring the back gate voltage to the underside of the dielectric layer under the channel through a metal or other conductive via. While the following sections will concentrate on a description of the sensor 31 with only a solution gate 39, it can be advantageous to operate the sensor with a back gate 36 only or with a combination of a solution gate 39 and back gate 36. By combining a solution gate 39 with a back gate 36 is may be possible to increase the sensitivity of the sensor to the analyte of interest.

Figure 8:
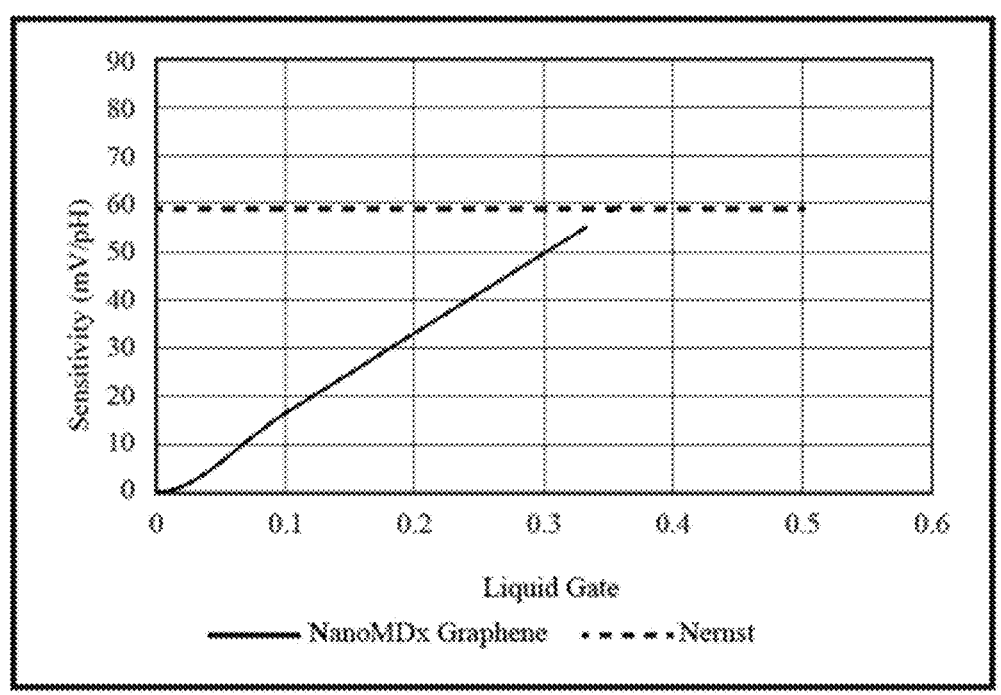
FIG. 8 is a graph of average sensitivity of a graphene FET ("GFET") calculated as a function of liquid gate potential.
Figure 9:
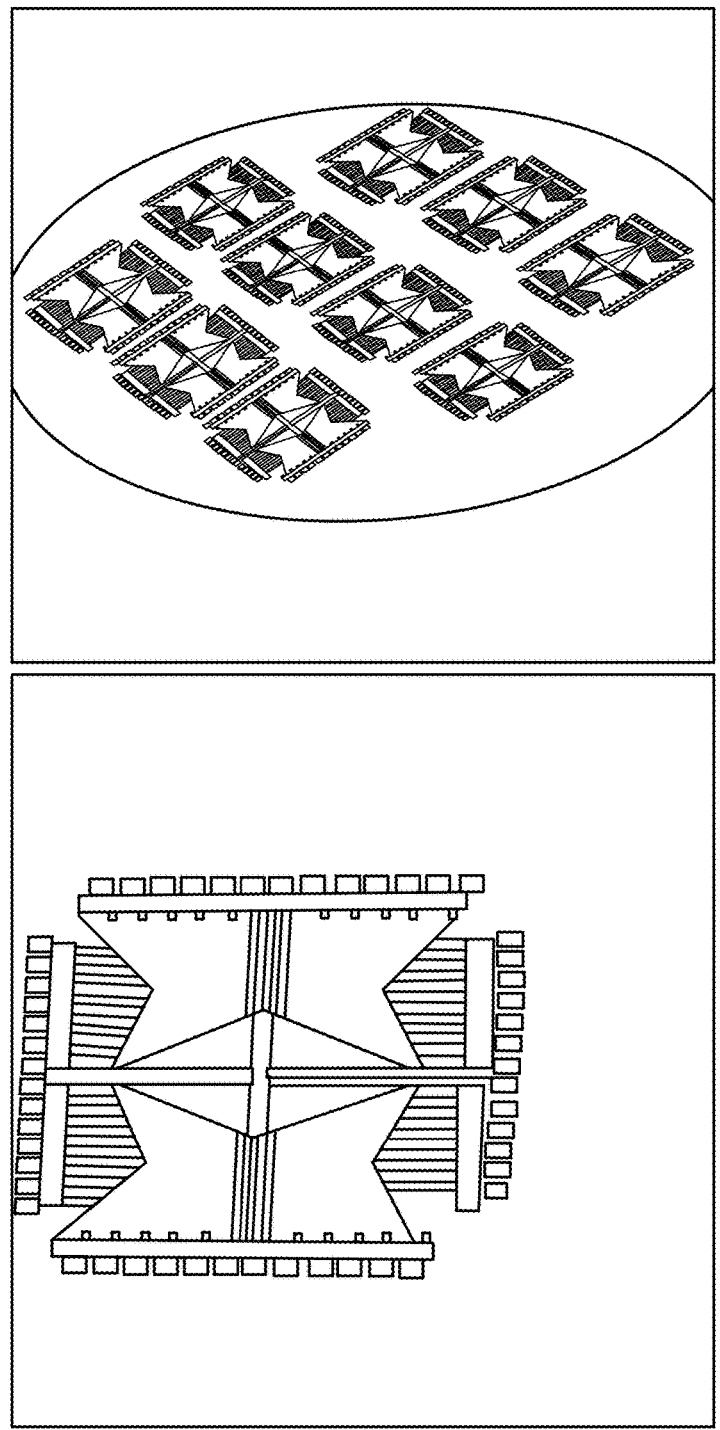
FIG. 9 is an illustration of a graphene field-effect transistor.

As shown in FIG. 8, an average sensitivity of a graphene FET ("GFET") calculated as a function of liquid or solution gate potential. The GFET of the present invention approaches the theoretical 59 mV/pH maximum for an ISFET type device (referred to as the Nernst limit).

Figure 10:
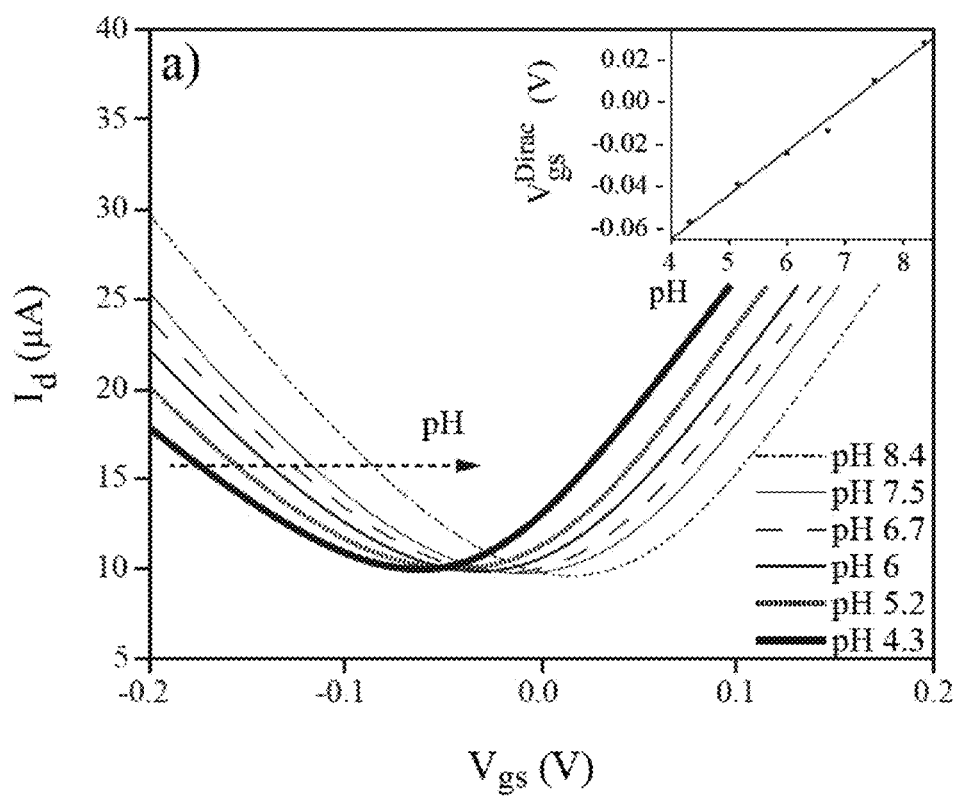
FIG. 10 is a graph of I-Vg curves for various pH values.
Figure 11:
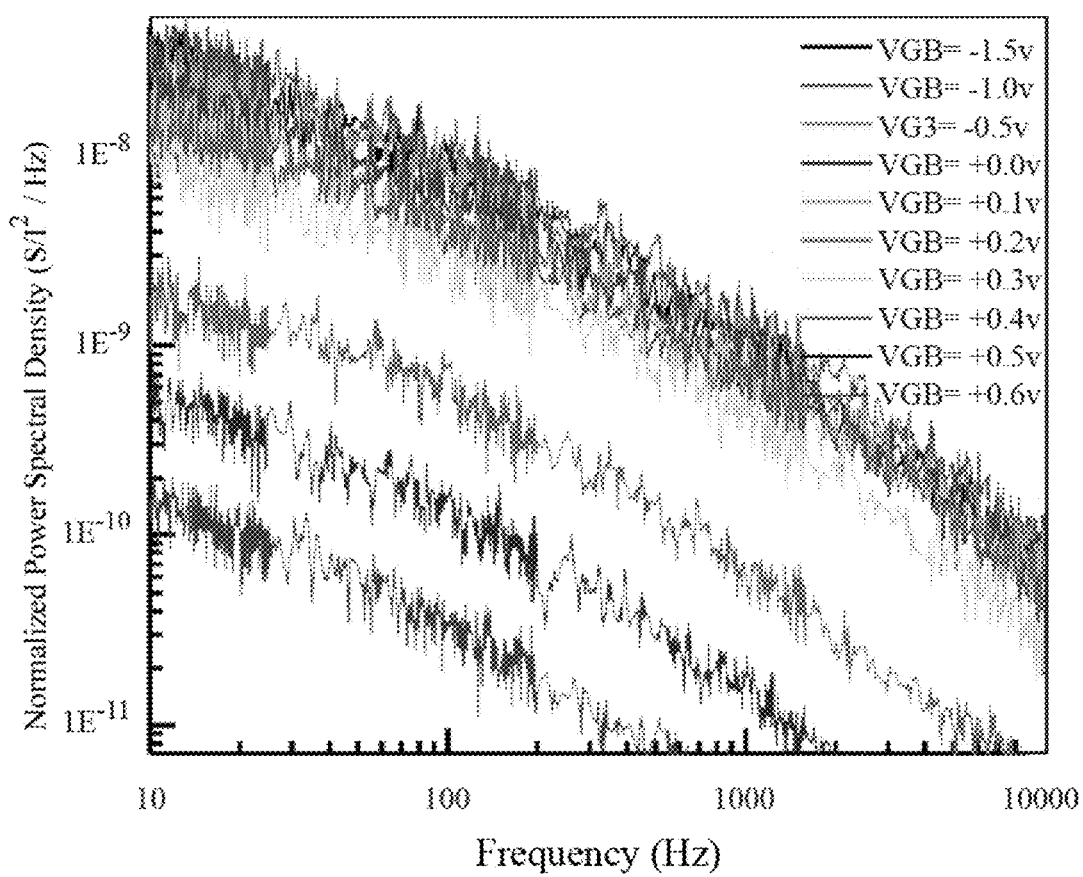
FIG. 11 is a graph of frequency vs. normalized power spectral density for a silicon ISFET.
Figure 12:
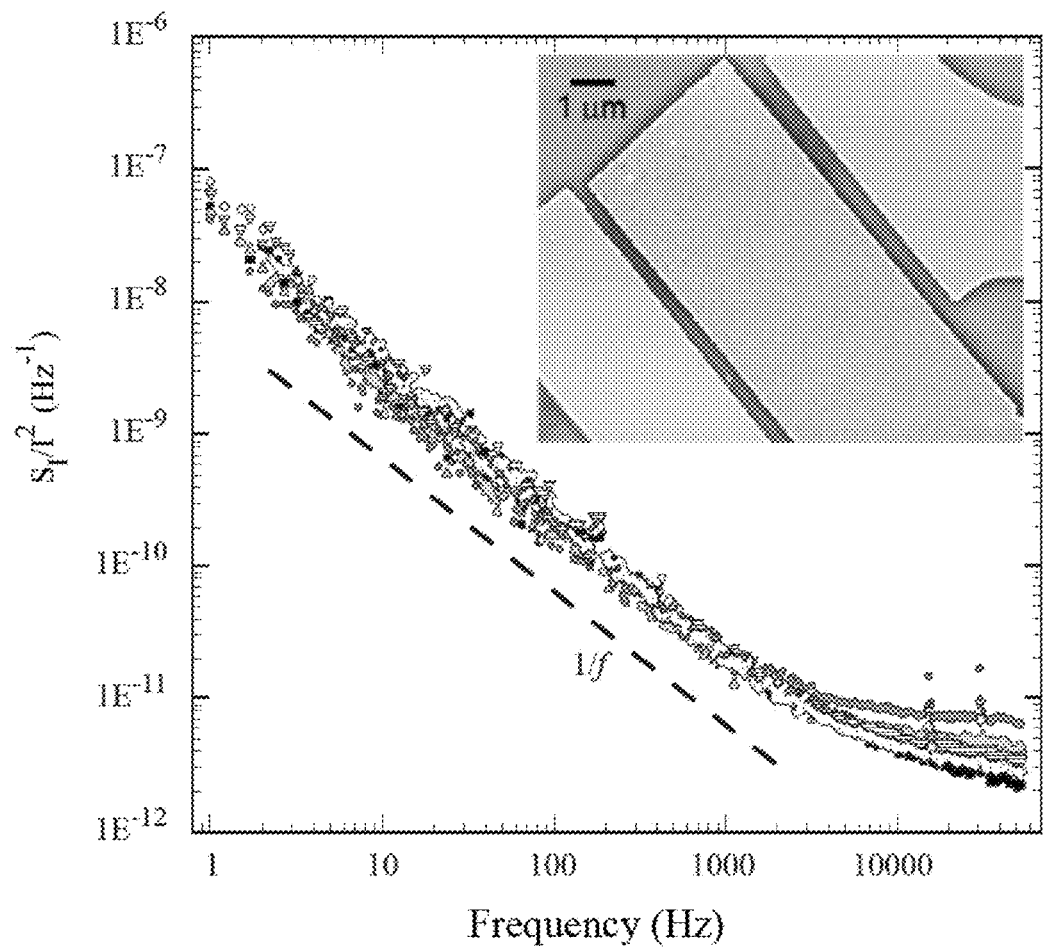
FIG. 12 is a graph of frequency vs. normalized power spectral density for a typical graphene FET.
Figure 13:
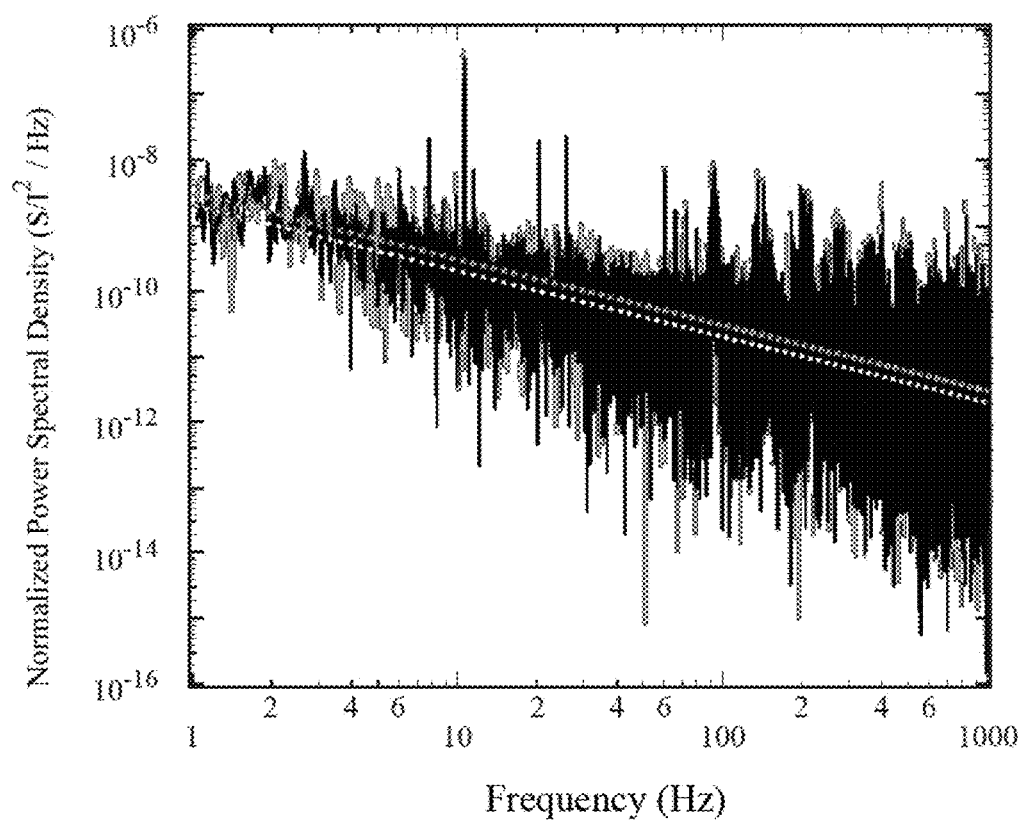
FIG. 13 is a graph of frequency vs. normalized power spectral density for a graphene FET of the present invention.
Figure 14:
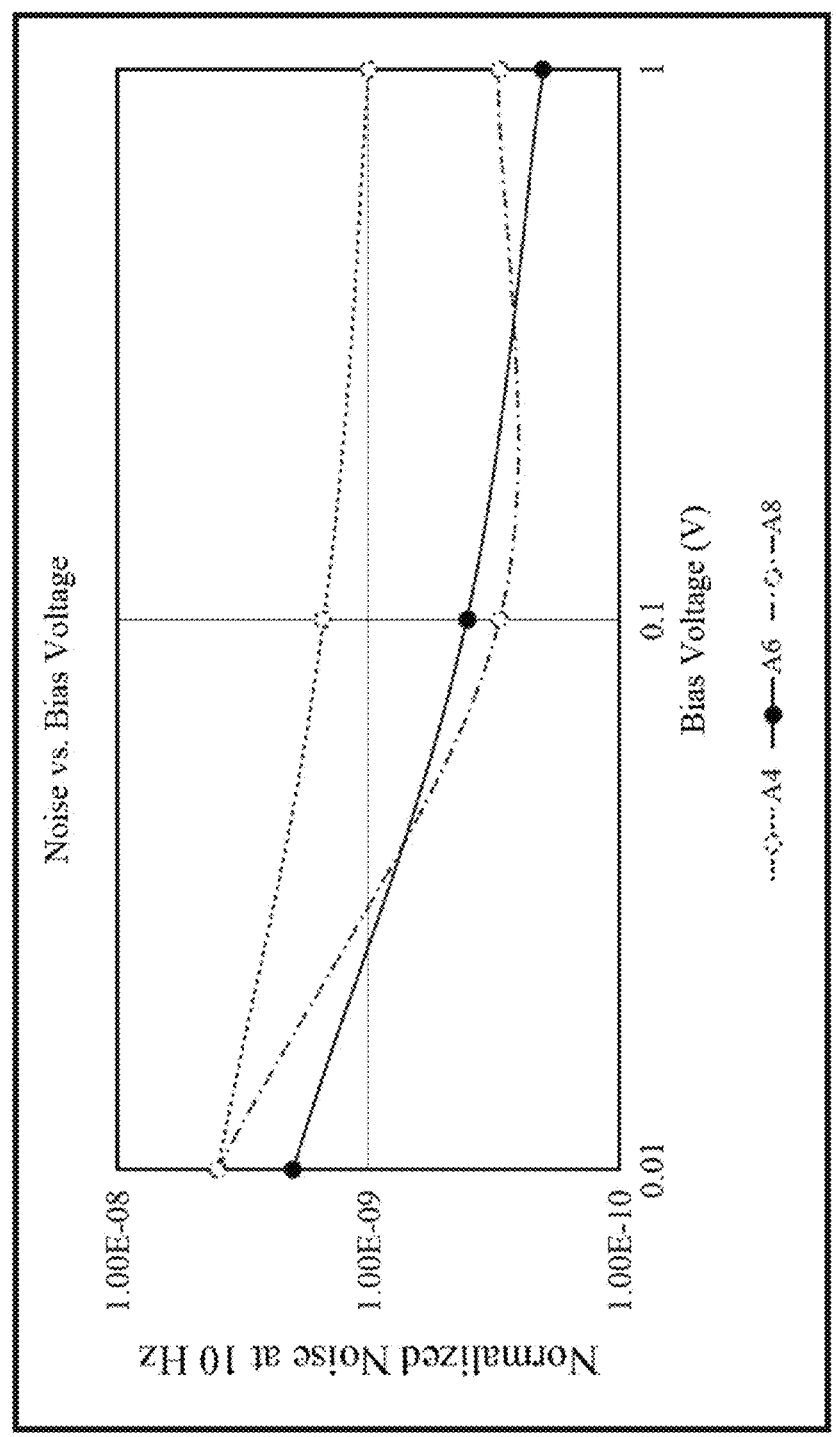
FIG. 14 is a graph of noise vs. bias voltage.
Figure 15:
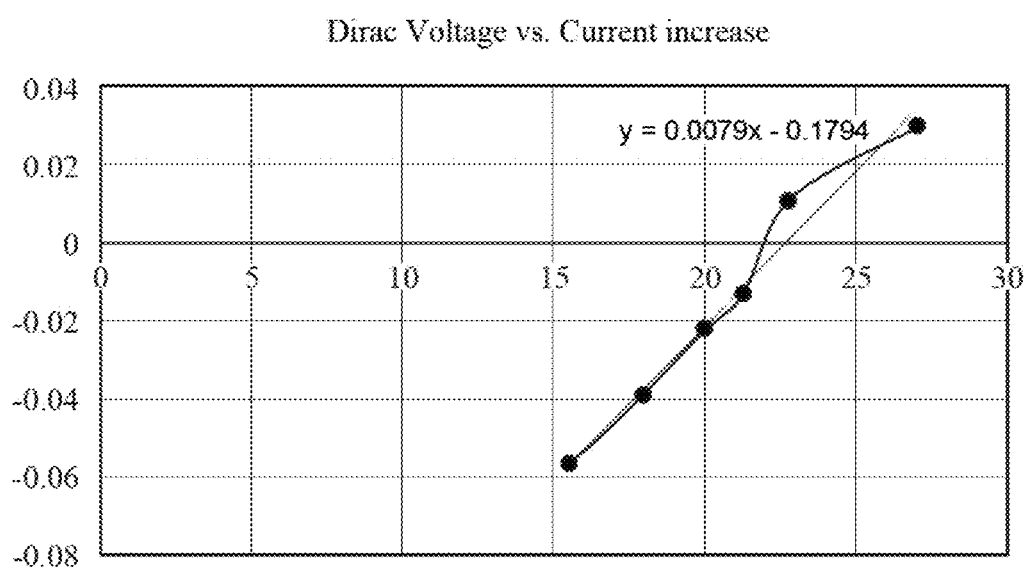
FIG. 15 is a graph of Dirac voltage vs. current increase.
Figure 16:
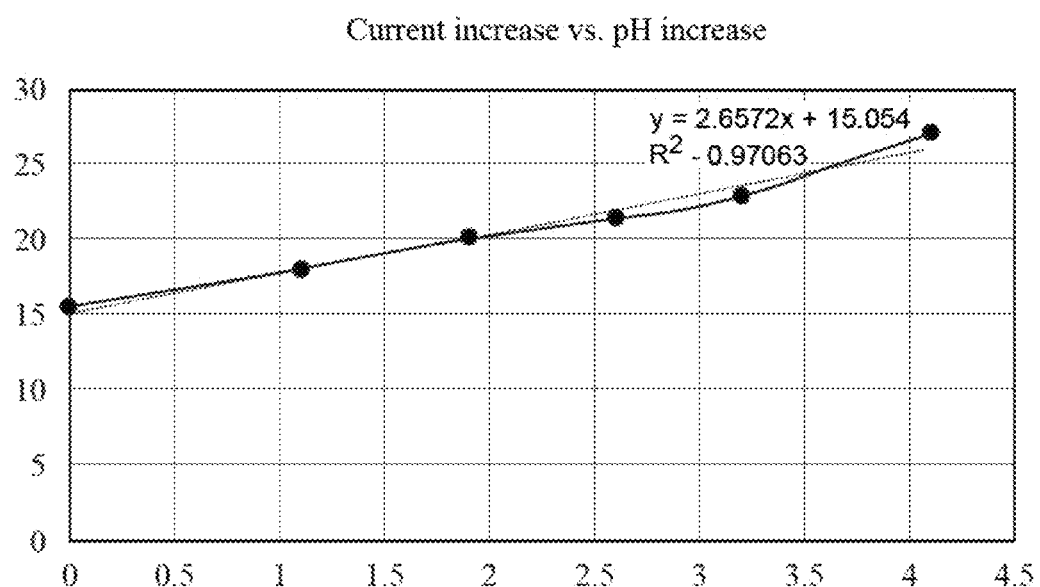
FIG. 16 is a graph of current increase vs. pH increase.

FIG. 10 illustrates the transfer characteristics of a 20×40 micron graphene-on-$SiO_2$ SGFET ("solution gated FET") at a constant drain-source voltage of $V_{ds}$=50 mV for different pH values.

Accordingly, when using the device for sequencing a nucleic acid sample, the target nucleic acid sample may be coupled to or in proximity with the graphene coated surface of the reaction zone. This template sequence may then be sequenced and/or analyzed by performing one or more of the following steps. For example, a primer, and/or a polymerase, e.g., an RNA and/or DNA polymerase, and/or one or more substrates, e.g. deoxynucleotide triphosphates dATP, dGTP, dCTP, and dTTP, may be added, e.g., sequentially, to the reaction chamber, such as after the hybridization reaction begins so as to induce an elongation reaction. Once the appropriate substrate hybridizes to its complement in the template sequence, there will be a concomitant change in the individual electrical characteristic voltage, e.g., the source-drain voltage (Vsd), measured as a result of the new local gating effect.

Hence, for every elongation reaction with the appropriate, e.g., complementary, substrate there will be a change in the characteristic voltage. For instance, as described herein, a field-effect device for nucleic acid sequencing and/or gene detection is disposed in a sample chamber of a flow cell, and a sample solution, e.g., containing a polymerase and one or more substrates, may be introduced to the sample solution chamber. In various embodiments, a reference electrode may be disposed upstream, downstream or in fluid contact with the field-effect device and/or the source and/or drain may themselves serve as electrodes, such as for hybridization detection, and gate voltage may be applied whenever needed.

Particularly, in an exemplary elongation reaction, polynucleotides are synthesized if the added substrate is complementary to the base sequence of the target DNA primer and/or template. If the added substrate is not complementary to the next available base sequence, hybridization does not occur and there is no elongation. Since nucleic acids, such as DNAs and RNAs, have a negative charge in aqueous solutions, hybridization resulting in elongation can be incrementally determined by the change in the charge density in the reaction chamber or well 38. And because the substrates are added sequentially, it can readily be determined which nucleotide bound to the template thereby facilitating the elongation reaction. Accordingly, as a result of elongation, the negative charge on the graphene gate surface, insulating film surface, and/or the sidewall surface of the reaction chamber will be increased. This increase may then be detected, such as a change in the gate-source voltage, as described in detail herein. By determining the addition of which substrate resulted in a signal of change in gate-source voltage, the base sequence identity of the target nucleic acid can be determined and/or analyzed.

More specifically, the field-effect transistor, such as for nucleic acid elongation and/or hybridization detection, may be associated with a buffered solution that is added to the reaction chamber, which can then be used to determine if an elongation reaction has taken place. Particularly, once the template is associated with the substrate, the reaction mixture containing a polymerase, e.g., a Taq polymerase, and a first nucleic acid substrate, e.g., a dATP, is added to the buffer solution to carry out the elongation reaction on or over the analyte-sensitive dielectric layer 35 or the graphene channel 33 coated insulating film of the reaction chamber surface. If the dATP is a complement to the next available reaction site in the isolated template a binding event, e.g., a hybridization reaction, will occur and the antisense strand of the growing sequence will be elongated, and detected by the GFET transistor.

For example, if adenine (A) is complementary to the base thymine (T) on the target template adjacent to the 3'-terminus of the nucleic acid template, an elongation reaction occurs, resulting in synthesis of one adenine. In such instance, the enzyme, Taq DNA polymerase, and the substrate may be washed away from the channel portion 33 and reaction chamber 38, and a buffer solution, e.g., a phosphoric acid buffer solution, e.g., having a pH of about 6, may be introduced on or over the graphene channel surface 33 or the analyte-sensitive dielectric layer 39 to measure changes in the source-drain voltage. If hybridization has occurred there will be a change in the source-drain voltage and it will be detected. However, if the dATP is not a match, there will be no hybridization, and if no hybridization, there will be no elongation. Consequently, a second reaction mixture containing another, different nucleotide substrate, e.g., dCTP and the enzyme polymerase, and the like will be added to the reaction chamber or well 38 under conditions suitable for hybridization, which if it occurs will be detected by the GFET. If not, then the steps will be repeated with the next substrate. These steps may be repeated until the nucleic acid sample has been completely sequenced. In various instances, the temperature within the reaction chamber may be controlled, for instance, it may be set to 74° C., such as by using a temperature sensor and/or a heater integrated in the field-effect device.

Consequently, if a hybridization reaction takes place there will be a resultant change to the threshold voltage, which will be increased, e.g., by 4 mV, from before the elongation reaction. The shift of the threshold voltage in the positive direction indicates that a negative charge was generated on or over the graphene channel surface 33. It can be understood from this that synthesis of one base caused by the elongation reaction was detectable as a change in threshold voltage. A second elongation reaction may then take place and be repeated until the entire target nucleic acid has been sequenced.

More particularly, in such a configuration as represented in the figures, the drain current of the transistor may be modulated by the electrical charge carried by the nucleotide molecules involved in the hybridization and/or sequencing reactions. For example, after a binding event, the charge in the reaction zone increases resulting in a change in the output current that may be measured. Such a measurement may be made in accordance with the following equation:

$$V_{THF} = V_{TH0} - \frac{Q_{com} + Q_0}{C_C + C_F}$$

Such as where $C_C$ represents the current at the control capacitor, and $C_F$ represents the current at the parasitic capacitor. $V_{THF}$ represents the effective threshold voltage of the transistor (Dirac point), and $V_{TH0}$ represents the native threshold voltage (original Dirac point). $Q_0$ represents the electric charge initially trapped in the floating gate, and $Q_{DNA}$ represents the total charge of hybridization complex.

For instance, a nucleic acid from a sample to be sequenced or representative of a probe to be targeted may be immobilized on the bottom surface or the sidewall of the sample solution well chamber 38. A Taq DNA polymerase and a nucleotide substrate may then be introduced to the sample solution chamber to induce an elongation reaction. As a result, DNAs may be synthesized along the surface in the vertical or lateral direction, e.g., in parallel to the surface of the graphene coated channel surfaces. In such an instance, as the source-drain current vs gate voltage characteristic changes by the electrostatic interaction with the charged particles (electrons) in the well, and the synthesis of the DNA is in the direction that is transverse or parallel to the graphene channel surface, this keeps the distance between the DNA and the electrons constant, thereby helping to maintain a constant electrostatic interaction. Thus, the base sequence of a template nucleic acid having a large base length can be sequenced and/or analyzed. In other embodiments, a nucleic acid probe may be immobilized on the surface of the reaction zone, as described above, and used in a hybridization reaction so as to detect genetic variation and/or the presence of a genetic disease.

In various instances, in order to conduct parallel analysis of a plurality of nucleic acid templates, the number of the transistors may be equal to or higher than the number and/or types of DNAs to be sequenced and/or analyzed. In certain instances, each nucleic acid template or probe may be an oligonucleotide or a fragment of DNA or RNA that may be constituted from about 100 to about 1000 bases, such as from 200 to about 800 bases, for instance, from about 300 or about 500 bases to about 600 or 700 bases or more or somewhere in between. However, in various instances, a fragment of nucleic acid having 100 bases or fewer may also be used.

Additionally, as indicated above, the device 10 may also be used in various different DNA/RNA hybridization reactions, such as for the purpose of determining a genetic variation and/or for detecting the presence of a genetic marker for a disease. In such an instance, a nucleic acid probe may be coupled to a bottom or side graphene coated or analyte-sensitive dielectric layer coated surface of the reaction chamber or well 38, per above. As indicated, the probe may be of any suitable length but in various instances from about 5 or 10 to about 1000 bases, such as from 20 or about 50 to about 700 or about 800 bases, for instance, from about 100 or about 200 bases to about 300 bases including about 400 or about 500 bases to about 600 or 700 bases or more or somewhere in between.

For instance, in one exemplary instance, a nucleic acid probe containing about 10 to 15 bases coding for a gene sequence of interest that has been previously amplified, such as by polymerase chain reaction (PCR), may be immobilized on the channel, analyte-sensitive dielectric layer or side surface of the reaction chamber 38 of the field-effect transistor. For example, once isolated and amplified, the base of the template may be modified so as to be attached to the graphene or analyte-sensitive dielectric coated surface, and/or may be coupled to a secondary substrate, such as a glass or plastic bead that has been chemically treated so as to be coupled therewith. Once immobilized, the reaction chamber containing the probes, either on a secondary substrate or directly coupled with a chamber surface, may be reacted with a sample solution containing a number genes including a target gene of interest to be measured such that when a nucleic acid probe having a complementary base sequence to the target gene is immobilized on the gate, gate insulating film or the sidewall surface of the sample solution well structure, or on a secondary substrate immobilized within the reaction chamber of the field-effect device for gene detection, the target gene hybridizes with the nucleic acid probe under appropriate reaction conditions and the target gene and the nucleic acid probe form a double strand, the result of which hybridization reaction may be detected.

A GFET array sets forth a two dimensional GFET sensor array chip that in this instance is based on a column and row design, although other designs are also possible. The system further includes a row and column decoder, as well as circuitry for performing the requisite sensing, detecting, and processing so as to measure the sensory data. Hence, also included is sensing, measurement, and other associated readout data.

Accordingly, in various instances, a one or two-dimensional GFET array, as described herein, may be fabricated on a microchip in accordance with the methods herein disclosed. In various instances, the array chip may include a number of GFET sensors that may be arranged in columns and/or rows. A typical number of sensors may include GFET sensor elements, described herein as "sensors," that may be arranged in a 16 sensor by 16 sensor column/row array configuration. As depicted, the array includes two columns, but typically may include sixteen columns, arranged side by side, where each column includes 16 rows. Particularly, each column of the array includes up to 16 sensors. Each column may be configured so as to include a current source $I_{SOURCE}$ that may be shared by all sensors of the column. However, in various other embodiments, each sensor may have its own current source, or the array itself may have a single current source. Additionally, each GFET sensor may include a GFET, as described above, having an electrically coupled source and/or drain and/or body, and may further include one or more switches, such as a plurality of switches S1 and S2 that may be configured so as to be responsive to one of the up to sixteen row select signals (RSEL, and it's complements). More particularly, a row select signal and its complement may be generated simultaneously to "enable" or select a given sensor of the selected column, and such signal pairs may be generated in some sequence to successively enable different sensors of the column, e.g., together or one at a time, such as sequentially. Other architectures may be employed to address the sensors—including architectures that may only require one access transistor per sensor.

A row decoder may also be provided as part of the system. In such an instance, the row decoder may be configured so as to provide up to sixteen pairs of complementary row select signals, wherein each pair of row select signals may be adapted so as to simultaneously or sequentially enable one sensor in each column so as to provide a set of column output signals from the array, e.g., based on the respective source voltages $V_{Sa}$ through $V_{Sb}$, etc. of the enabled row of GFETs. The row decoder may be implemented as a conventional four-to-sixteen decoder (e.g., a four-bit binary input $ROW_1$-$ROW_4$ to select one of $2^4$ outputs). The set of column output signals $V_{Sa}$ through $V_{Sb}$ for an enabled row of the array is applied to switching logic, which may be configured to include up to sixteen transmission gates Sa through Sb (e.g., one transmission gate for each output signal).

As above, each transmission gate of the switching logic may be implemented using an n-channel or p-channel MOSFET, in a bottom or top gate configuration, or both to ensure a sufficient dynamic range for each of the output signals $V_{Sa}$ through $V_{Sb}$. The column decoder, like the row decoder, may be implemented as a conventional four-to-sixteen decoder and may be controlled via the four-bit binary input $COL_1$-$COL_4$ to enable one of the transmission gates Sa through Sb of the switching logic at any given time, so as to provide a single output signal $V_S$ from the switching logic. This output signal $V_S$ may be applied to a 10-bit analog to digital converter (ADC) to provide a digital representation $D_1$-$D_{10}$ of the output signal $V_S$ corresponding to a given sensor of the array.

As noted earlier, individual GFETs and arrays of GFETs such as those discussed above may be employed as sensing devices in a variety of applications involving chemistry and biology. In particular, such GFETs may be employed as pH sensors in various processes involving nucleic acids such as DNA. In general, the development of rapid and sensitive nucleic acid hybridization and sequencing methods, as herein described, e.g., utilizing automated DNA sequencers, may significantly advance the understanding of biology.

It should be noted, that with respect to the various arrays disclosed herein according to various embodiments of the present disclosure may be fabricated according to conventional CMOS fabrication techniques, as described above, as well as modified CMOS fabrication techniques (e.g., to facilitate realization of various functional aspects of the GFET arrays discussed herein, such as additional deposition of graphene and/or other materials, process steps to mitigate trapped charge, etc.) and other semiconductor fabrication techniques beyond those conventionally employed in typical CMOS fabrication (e.g BiCMOS). Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one embodiment, the array includes 512 columns with corresponding column bias/readout circuitry (one for each column), wherein each column includes geometrically square sensors, each having a size of approximately 9 micrometers by 9 micrometers (e.g., the array may be up to 512 columns by 512 rows). In various instances, the entire array (including sensors together with associated row and column select circuitry and column bias/readout circuitry) may be fabricated on a semiconductor die as an application specific integrated circuit (ASIC), structured ASIC, or as a field programmable gate array, such as having dimensions of approximately 7 millimeters by 7 millimeters.

Various power supply and bias voltages useful for array operation are provided to the array via electrical connections (e.g., pins, metal pads) and labeled for simplicity in block as "supply and bias connections." The array may also include a row select shift register, one or more, e.g., two sets of column select shift registers, and one or more, e.g., two, output drivers, which output drivers are configured to provide two parallel output signals from the array, $V_{outa}$ and $V_{outb}$, representing sensor measurements. The various power supply and bias voltages, control signals for the row and column shift registers, and control signals for the column bias/readout circuitry may be provided by an array controller, which controller may also read the output signals $V_{outa}$ and $V_{outb}$ (and other optional status/diagnostic signals) from the array.

Configuring the array such that multiple regions (e.g., multiple columns) of the array may be read at the same time via multiple parallel array outputs (e.g., $V_{outa}$ and $V_{outb}$) facilitates increased data acquisition rates.

It should be noted that, in various embodiments of the array, one or more of the columns, e.g., the first and last columns, as well as the first and/or last sensors of each of the columns may be configured as "reference" or "dummy" sensors. For instance, the dummy sensors of an array, e.g., the topmost metal layer of each dummy sensor may be tied to the same metal layer of other dummy sensors and may be made accessible as a terminal of the chip, which in turn may be coupled to a reference voltage $V_{REF}$. Such reference voltage $V_{REF}$ may be applied to the bias/readout circuitry of respective columns of the array. In some exemplary implementations, preliminary test/evaluation data may be acquired from the array based on applying the reference voltage $V_{REF}$ and selecting and reading out dummy sensors, and/or reading out columns based on the direct application of $V_{REF}$ to respective column buffers (e.g., via the CAL signal), to facilitate offset determination (e.g., sensor-to-sensor and column-to-column variances) and array calibration. The calibration data can be stored for each sensor location either just prior to a sequencing session, or preferentially at the end of the device manufacturing process. The calibration data can be stored on-chip in non-volatile memory.

A more detailed description of a system for analysis of biological and chemical materials is set forth in van Rooyen et al., U.S. Patent Publication Number 20140371110 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Patent Publication Number 20140309944 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Patent Publication Number 20140236490 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Pat. No. 9,014,989 for Bioinformatics Systems, Apparatuses, and Methods Executed On An Integrated Circuit Processing Platform, which is hereby incorporated by reference in its entirety. A more detailed description of a system for analysis of biological and chemical materials is set forth in U.S. Provisional Application No. 61/826,381, titled System and Method for Computation Geneomic Pipeline, filed May 22, 2013, which is hereby incorporated by reference in its entirety. A more detailed description of a system for analysis of biological and chemical materials is set forth in U.S. Patent Publication Number 20150339437, for Dynamic Genome Reference Generation For Improved NGS Accuracy And Reproducibility, filed Feb. 24, 2015, which is hereby incorporated by reference in its entirety. A description of a GFET is set forth in van Rooyen, U.S. Provisional Patent Application No. 62/094,016, filed on Dec. 18, 2014, for Graphene FET Devices, Systems, And Methods Of Using The Same For Sequencing Nucleic Acids, which is hereby incorporated by reference in its entirety. A description of a GFET is set forth in Hoffman et al., U.S. Provisional Patent Application No. 62/130,594, filed on Mar. 9, 2015, for Chemically Sensitive Field Effect Transistor, which is hereby incorporated by reference in its entirety. A more detailed description of a GFET is set forth in Hoffman et al., U.S. Provisional Patent Application No. 62/206,228, filed on Aug. 17, 2015, for Chemically Sensitive Field Effect Transistor, which is hereby incorporated by reference in its entirety. A more detailed description of a GFET is set forth in Hoffman et al., U.S. Provisional Patent Application No. 62/199,987, filed on Aug. 1, 2015, for Chemically Sensitive Field Effect Transistor, which is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

REFERENCE NUMERALS

10 System
20 Fluidics component
21 Fluid
22 Bead
23 DNA strand
30 Array
31 Sensor
32 Chemically-sensitive field-effect transistor
33 Channel
34 Conductive element
35 Analyte-sensitive dielectric layer
36 Back gate
37 Lower dielectric layer
38 Well structure
39 Solution or Top gate
40 Circuitry component
50 Computing component

We claim as our invention the following:

1. A chemically-sensitive field effect transistor having a multi-layered structure for performing a sequencing reaction involving the sequencing of strands of nucleic acids, the field effect transistor, comprising:
    a substrate layer having an extended body;
    a first insulating layer positioned above the extended body of the substrate layer;
    a second insulating layer positioned above the first insulating layer;
    a source electrode and a drain electrode each having a top surface and a bottom surface, the top surface separated from the bottom surface by opposing outer and inner side portions, each of the opposed side portions and each of the bottom surfaces of the source and drain electrodes being disposed within the first insulating layer, the source electrode being separated from the drain electrode by a distance;
    a graphene layer positioned between the first insulating layer and second insulating layer and extending between the outer side portion of the source electrode and the outer side portion of the drain electrode thereby forming a channel between the source electrode and drain electrode, the graphene layer contacting the top surface of the source electrode and drain electrode; and
    a reaction chamber formed by a well structure provided in the second insulating layer, the well structure having an opening at a top surface of the second insulating layer and extending toward the graphene layer the graphene layer forming a bottom layer of the reaction chamber, the reaction chamber configured for receiving and retaining one or more reactants therein for performing the sequencing reaction.

2. The chemically-sensitive field effect transistor according to claim 1, wherein the multi-layered structure is configured so as to shift or change a characteristic of an I-V curve or an I-Vg curve in response to a chemical reaction occurring within the reaction chamber of the well of the chemically-sensitive field effect transistor.

3. The chemically-sensitive field effect transistor according to claim 2, further comprising an analyte-sensitive dielectric layer.

4. The chemically-sensitive field effect transistor according to claim 3, wherein the analyte-sensitive dielectric layer comprises an oxide layer.

5. The chemically-sensitive field effect transistor according to claim 3, wherein the second insulating layer is composed of a polymer, polyimide, BCB, inorganic material, silicon oxide, a silicon nitride, a silicon oxynitride or a silicon carbide.

6. The chemically-sensitive field effect transistor according to claim 1, wherein the conductive source and the conductive drain are each comprised of a copper material, an aluminum material, a platinum material, or a gold material.

7. The chemically-sensitive field effect transistor according to claim 6, wherein the channel has a thickness of 50 nanometers or less.

8. A chemically-sensitive field effect transistor having a multi-layered structure for performing a biological reaction involving one or more of a deoxyribonucleic acid, a ribonucleic nucleic acid, and a protein, the field effect transistor comprising:
    a substrate layer having an extended body;
    a first insulating layer positioned above the extended body of the substrate layer;
    a source electrode and a drain electrode positioned in or over the first insulating layer, the source electrode separated from the drain electrode by a distance;
    a second insulating layer positioned above the first insulating layer and proximate the source and drain electrodes;
    a graphene layer positioned between the first and second insulating layers and extending between the source and drain electrodes thereby forming a channel between the source electrode and drain electrode; and
    a reaction chamber formed by a well structure provided in the second insulating layer, the well structure having an opening at a top surface of the second insulating layer and extending toward the graphene layer, the graphene layer substantially extending between an outer side portion of the drain electrode and an outer side portion of the source electrode and forming a bottom layer within the reaction chamber, the reaction chamber configured for receiving and retaining one or more of a deoxyribonucleic acid, a ribonucleic nucleic acid, and a protein therein for performing the biological reaction.

9. The chemically-sensitive field effect transistor according to claim 8, wherein the multi-layered structure is configured so as to shift an I-V curve or an I-Vg curve in response to the biological reaction occurring within the chamber of the well of the chemically-sensitive field effect transistor.

10. The chemically-sensitive field effect transistor according to claim 9, wherein a length of the channel from the source to the drain ranges from 0.05 micron to 2 microns, and a width of the channel ranges from 0.05 micron to 5 microns.

11. The chemically-sensitive field effect transistor according to claim 10, further comprising an analyte-sensitive dielectric layer.

12. The chemically-sensitive field effect transistor according to claim 8, wherein the biological reaction comprises a member selected from the group consisting of a nucleic acid sequencing reaction, a nucleic acid hybridization reaction, and a protein detection reaction, and the chemically-sensitive field effect transistor is configured for detecting a result of the reaction.

13. A chemically-sensitive field effect transistor having a multi-layered structure for performing a biological reaction involving fluidic reagents within a fluid, the field effect transistor comprising:
- a substrate layer having an extended body;
- a first insulating layer positioned above the extended body of the substrate layer;
- a source electrode and a drain electrode positioned in or over the first insulating layer, the source electrode and the drain electrode being separated by a distance;
- a second insulating layer positioned above the first insulating layer and proximate the source and drain electrodes;
- a graphene layer positioned between the first and second insulating layers and substantially extending between an outer side portion of the drain electrode and an outer side portion of the source electrode to form a channel between the source and drain electrodes; and
- a reaction chamber formed by a well structure provided in the second insulating layer, the well structure having an opening therein, the opening defined by opposed side portions and a bottom formed at least by the graphene layer, the reaction chamber configured for receiving and retaining one or more of the reagents in a fluid therein for performing a biological reaction.

14. The chemically-sensitive field effect transistor according to claim 13, wherein the one-dimensional transistor material or two-dimensional transistor material selected from the group consisting of a single layer planar graphene, black phosphorous, silicene, borophene, tungsten disulfide, germanane, nickel HITP, stanene and Mxenes.

15. The chemically-sensitive field effect transistor according to claim 13, further comprising an analyte-sensitive dielectric layer.

16. The chemically-sensitive field effect transistor according to claim 15, wherein the analyte-sensitive dielectric layer comprises an oxide layer.

17. The chemically-sensitive field effect transistor according to claim 13, wherein the biological reaction involves a biological material selected from the group consisting of a nucleotide, nucleic acid, and a protein, and the chemically-sensitive field effect transistor is configured for detecting the biological material.

18. A chemically-sensitive field effect transistor having a multi-layered structure for performing a biological reaction, the field effect transistor comprising:
- a substrate layer, the substrate layer having an extended body;
- a first insulating layer positioned above the extended body of the substrate layer;
- a source electrode and a drain electrode positioned in the first insulating layer, the source electrode separated from the drain electrode by a distance;
- a second insulating layer positioned above the first insulating layer and proximate the source and drain electrodes;
- a graphene layer positioned between the first and second insulating layers and substantially extending between an outer side portion of the source electrode and an outer side portion of the drain electrodes to form a channel there-between; and
- a reaction chamber formed by a well structure provided in the second insulating layer, the well structure having an opening, the opening including opposing side portions and a bottom formed by at least the graphene layer, the reaction chamber configured for receiving and retaining one or more reactants therein for performing the biological reaction.

19. The chemically-sensitive field effect transistor according to claim 18, wherein the multi-layered structure is configured so as to shift or change a characteristic of an I-V curve or an I-Vg curve in response to the biological reaction occurring within the reaction chamber of the well of the chemically-sensitive field effect transistor.

20. The chemically-sensitive field effect transistor according to claim 19, further comprising an analyte-sensitive dielectric layer.

21. The chemically-sensitive field effect transistor according to claim 20, wherein the analyte-sensitive dielectric layer comprises an oxide layer.

22. The chemically-sensitive field effect transistor according to claim 19, wherein the biological reaction involves a biological material selected from the group consisting of a nucleotide, nucleic acid, and a protein, and the chemically-sensitive field effect transistor is configured for detecting the biological material.

* * * * *

UNITED STATES PATENT AND TRADEMARK OFFICE
CERTIFICATE OF CORRECTION

PATENT NO. : 10,429,342 B2  
APPLICATION NO. : 14/963253  
DATED : October 1, 2019  
INVENTOR(S) : Paul Hoffman, Mitchell Lerner and Pieter Van Rooyen Page 1 of 1

It is certified that error appears in the above-identified patent and that said Letters Patent is hereby corrected as shown below:

On the Title Page

"(72) Inventors: Paul Hoffman, San Diego, CA (US); Mitchell Lerner, San Diego, CA (US); Pieter Van Rooyen, San Diego, CA (US);" should read "(72) Inventors; Paul Hoffman, San Diego, CA (US); Mitchell Lerner, San Diego, CA (US); Pieter Van Rooyen, San Diego, CA (US); Brett R. Goldsmith, San Diego, CA (US);"

Signed and Sealed this  
Twenty-fourth Day of March, 2020

Andrei Iancu  
*Director of the United States Patent and Trademark Office*